(12) United States Patent
Evans

(10) Patent No.: US 9,718,768 B2
(45) Date of Patent: Aug. 1, 2017

(54) SYSTEM FOR PURIFYING, PRODUCING AND STORING BIOMOLECULES

(75) Inventor: David Evans, St. Asaph (GB)

(73) Assignee: ADC Biotechnology Ltd., St. Asaph, Denbighshire (GB)

( * ) Notice: Subject to any disclaimer, the term of this patent is extended or adjusted under 35 U.S.C. 154(b) by 571 days.

(21) Appl. No.: 14/111,305

(22) PCT Filed: Apr. 12, 2012

(86) PCT No.: PCT/GB2012/050812
§ 371 (c)(1),
(2), (4) Date: Oct. 11, 2013

(87) PCT Pub. No.: WO2012/140433
PCT Pub. Date: Oct. 18, 2012

(65) Prior Publication Data
US 2014/0037961 A1    Feb. 6, 2014

(30) Foreign Application Priority Data

Apr. 12, 2011 (GB) .................................. 1106173.6

(51) Int. Cl.
| | | |
|---|---|---|
| C07K 9/00 | (2006.01) |
| C07C 319/28 | (2006.01) |
| A61K 47/48 | (2006.01) |
| B01J 20/287 | (2006.01) |
| B01J 20/32 | (2006.01) |
| C07K 1/22 | (2006.01) |
| C07C 59/347 | (2006.01) |
| C07C 323/58 | (2006.01) |
| C07K 17/02 | (2006.01) |

(52) U.S. Cl.
CPC ...... *C07C 319/28* (2013.01); *A61K 47/48438* (2013.01); *A61K 47/48584* (2013.01); *B01J 20/287* (2013.01); *B01J 20/3212* (2013.01); *B01J 20/3219* (2013.01); *B01J 20/3248* (2013.01); *B01J 20/3251* (2013.01); *B01J 20/3274* (2013.01); *C07C 59/347* (2013.01); *C07C 323/58* (2013.01); *C07K 1/22* (2013.01); *C07K 17/02* (2013.01); *Y10T 428/2982* (2015.01)

(58) Field of Classification Search
None
See application file for complete search history.

(56) References Cited

FOREIGN PATENT DOCUMENTS

| | | |
|---|---|---|
| JP | 10246729 | 7/2000 |
| WO | 01/99378 A3 | 12/2001 |
| WO | 2005/123971 A3 | 12/2005 |

OTHER PUBLICATIONS

Zhang et. al. Solvent-free liquid-phase synthesis of polyhydrouioline derivates under microwave irradiation, ARKIVOC 2007 (xiii) 79-86.*
Zhang et al. ARKIVOC 2007 (xiii) 79-86.*
Rader et al. PNAS 5396-5400, Apr. 29, 2003, vol. 100 No. 9.*
Search and Examination, Intellectual Property Office, United Kingdom, Aug. 23, 2012, pp. 1-6.
International Search Report and Written Opinion, International Application No. PCT/GB2012/050812, ADC Biotechnology Ltd., Sep. 6, 2012, pp. 1-13.
Zhang, Xiao-Lan. Solvent-Free Liquid Phase Synthesis of PolyHydroquinoline Derivatives Under Microwave Irradiation. ARKIVOC, 2007, 79-86, (xiii), ARKAT USA, Inc., USA.
Rader, Christopher. Chemically Programmed Monoclonal Antibodies for Cancer Therapy: Adaptor Immunotherapy Based on a Covalent Antibody Catalyst. Proc Nat Acad Sci, 2003, 5396-5400, 100(9), National Academy of Sciences, USA.
Gambero, Alessandra. Use of Chemically Modified Silica With B-Diketoamine Groups for Separation of A-Lactoalbumin From Bovine Milk Whey by Affinity Chromatography. J Colloid Interface Sci, 1997, 313-316, 185, Academic Press, USA.

* cited by examiner

*Primary Examiner* — Jeanette Lieb
(74) *Attorney, Agent, or Firm* — Chavous Intellectual Property Law LLC

(57) ABSTRACT

The invention relates to a lock-release method to be applied to biomolecules, such as antibodies, to improve the purification, production, stability and storage of biomolecules. A biomolecule is covalently bound to a polymer support comprising a diketone group so that the biomolecule can be purified, produced and/or stored before being released from the support. The diketone group of the polymer support is a 1,3-ketoester, 1,3-ketothioester or 1,3-ketoamide is a group of Formula (1): $R^1$ is an optionally substituted hydrocarbyl, perhalogenated hydrocarbyl, or a heterocyclyl group; Y is hydrogen, an optionally substituted hydrocarbyl, or a heterocyclyl group; X is —O, —$NR^2$ or —S, wherein the free valence of —O, —$NR^2$ or —S is bonded to the support optionally via a linker; and $R^2$ is hydrogen, an optionally substituted hydrocarbyl, or a heterocyclyl group. The invention also relates to a polymer support comprising the diketone group.

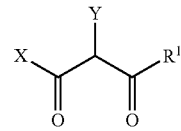

Formula 1

15 Claims, 10 Drawing Sheets

Y axis units = Abs (A450nm)

SYSTEM FOR PURIFYING, PRODUCING AND STORING BIOMOLECULES

This is an application that entered the national stage pursuant to 35 U.S.C. §371 from International Appl. Ser. No. PCT/GB2012/050812, which was filed on Apr. 12, 2012 and claims the benefit of foreign priority to GB Appl. Ser. No. 1106173.6, which was filed on Apr. 12, 2011, both applications being hereby incorporated by reference in their entireties.

The invention relates to a 'lock-release' concept to be applied to biomolecules to improve the purification, production, stability and storage of biomolecules. In particular, the invention relates to covalently binding a biomolecule to a polymer support comprising a diketone group so that the biomolecule can be purified, produced and/or stored before being released from the support.

BACKGROUND

A number of methods can be used to purify antibodies and other biomolecules. Purification is performed in solution. Tangential Flow Filtration (TFF) and Affinity Chromatography are commonly employed techniques which retrieve antibodies or other biomolecules from crude process liquors. Size Exclusion Chromatography and Ion Exchange Chromatography are further purification techniques which concentrate and or purify process liquors containing biomolecules. However, all these techniques are themselves wasteful in terms of generating large volumes of waste.

In Tangential Flow Filtration the biomolecule can be retained on a semi-permeable membrane (retentate) not through a chemical bond but via pressure or intermolecular forces. Small molecular weight contaminants are not retained on the membrane and are removed as a permeate stream (filtrate). These contaminants typically include additives purposefully introduced to the process stream. These additives create a stable environment for the biomolecule during the purification process (e.g. buffer salts, detergents, disaccharide stabilisers, preservatives, etc.). Once the biomolecule has been retained it is washed off the membrane with a buffer. This technique has several limitations, which include:

Poor affinity of the biomolecule for membrane (some product is lost in filtrate it it is not retained)
Biomolecule is subject to trans membrane pressure (TMP) which can cause undesired aggregation
Contamination of process liquor due to leachables from TFF membrane
Loss of biomolecule to membrane through 'blinding' (if it binds it cannot be removed and further separation becomes increasing difficult)
Fluctuations in retained biomolecule concentration on membrane can lead to the biomolecule exceeding its solubility limit (which leads to precipitation and loss to the membrane)
Effectiveness of process is compromised by minute changes in pH and ionic strength
Loss of product through dead volume and pipework (because the biomolecule is not removed in a concentrated slug of solvent)
Poor selectivity
No differentiation between active biomolecule and fragments or aggregates of the biomolecule
Requires specialist equipment with high cost association that is complicated to set up Alternatively, a biomolecule may be purified by affinity purification. Affinity chromatography is based on attaching a ligand to chromatography media, such as an agarose support. For example, to purify antibodies using affinity chromatography a ligand such as Protein A or Protein G can be employed. These ligands have a high affinity for antibodies but do not form a chemical bond to the antibody. Instead they form weak, temporary interactions which are hypersensitive to changes in pH, temperature, media and physical agitation.

Affinity chromatography is often seen as a last resort within pharmaceutical and biomolecule manufacturing and purification due to the high costs associated with operations. These costs accrue due to the cost of preparing the Protein A and Protein G ligands and attaching them to the chromatography media in such a way that affinity is still inferred. As such affinity media are expensive.

Furthermore, the loading of the chromatography media (essentially how much biomolecule, e.g. an antibody, may be attached to the support per gram) is very low; typically micromoles ($\mu M$) per gram. To manufacture Kgs of antibody at commercial scale, the cost of the chromatography media required would be prohibitive. Another disadvantage is that Protein A and Protein G affinity media are highly cross-linked Agarose supports which are easily broken by stirring or any form of agitation. Particulates arising from broken beads are a source of contamination and must also be removed from the process liquor during purification.

Many biomolecules are stored at low temperatures such as between 1° C. to 5° C. for short periods or frozen at temperatures below −20° C. for prolonged periods. Many biomolecules are prone to degradation by changes in temperature (the so-called freeze-thaw issue). For example, storing an antibody in a concentrated form in solution, where the antibody has the ability to interact and adopt different conformational positions, can lead to it losing activity. Storing in solution may also increase the risk of environmental exposure to microbial contamination and or endotoxins which is known as a detrimental issue.

An alternative technique for processing biomolecules is solid phase synthesis. This technique can be used in the manufacture of peptides, oligonucleotides and oligosaccharides.

Antibodies—typically used as therapeutic or diagnostic agents—are difficult to make and purify, with low-yielding manufacturing steps & wasteful processes.

At present, antibodies are manufactured by fermentation processes using batch bioreactors. A typical concentration of an antibody process stream is around 0.1% w/v. Therefore, within antibody production there are huge volumes of process liquors that require purification and eventual disposal of the waste generated for such processing. As such, 1 kg of antibody may need a large facility with 1000 liter reactors and associated ancillary equipment. For high potency antibody-based drugs such as Antibody Drug Conjugates (ADCs) the plant needs to be operated within a very high level of airborne containment (typically <50 nano gramme/$m^3$ air measured over a standard 8 hr work day) to prevent exposure of plant operators. Most existing ADC facilities are only able to operate at 50-100 liters scale, limiting the production batch size to 100 s of grammes at very high cost per gramme. For supply of launched products, which may require 10 s to 100 s of kilograms of drug, the problem is multiplied at least ten-fold. Furthermore in using this technique it is not unknown for an expensive batch of antibody to be lost through, for example, an operator error or unforeseen failure of a piece of equipment.

It is therefore an aim of the present invention to provide a system that would reduce the amount of biomolecules lost during processing, purification and/or storage of biomolecules. Ideally such a system would make it physically difficult to lose biomolecules during processing, purification and/or storage. Ideally the system would be highly selective for the biomolecule.

It is also an aim of the present invention to provide a system for processing, purifying and/or storing biomolecules that would not alter the integrity or biological activity of the biomolecule. Ideally, the system would not modify the biomolecule or alter its 3D structure. It is also an aim of the present invention to provide a system for processing, purifying and/or storing biomolecules that would reduce the cost of processing, purification and/or storage of biomolecules. Ideally such a system would be suitable for retrofitting into a manufacturing plant and would not require the use of expensive equipment, thus reducing capital expenditure. Ideally, such a system would be scalable to meet the demands of commercial manufacturing aspirations.

It is also an aim of the present invention to provide a system for processing, purifying and/or storing biomolecules faster and more simply than the prior art. Ideally the system would reduce waste produced from processing, purifying and/or storing biomolecules and therefore reduce the environmental impact. Ideally such a system would produce robust and reproducible results. Ideally such a system would be easy to operate without specialist knowledge. Ideally the system would be applicable to both batch and flow processing techniques.

It is also an aim of the present invention to provide a system for storing biomolecules in a safe, concentrated and contained manner for short or prolonged periods. Additionally, an aim of the present invention is to provide a system that allows the release of the immobilised biomolecule on demand.

This invention provides a system that achieves one or more of the above aims.

SUMMARY OF THE INVENTION

The present invention relates to methods and compositions for immobilising a biomolecule on a derivatised support. The support is derivatised with groups independently selected from 1,3-ketoesters, 1,3-ketothioesters or 1,3-ketoamides. The 1,3-ketoesters, 1,3-ketothioesters or 1,3-ketoamide groups are highly selective for primary amines and react with primary amines on biomolecules to form an enamine bond. This results in the biomolecule being immobilised on the derivatised support through a covalent bond. Once immobilised the biomolecule can be subjected to chemical reactions and/or washed. The immobilised biomolecule can be purified by washing away unwanted reagents, by-products and impurities. The biomolecule can be released from the derivatised support by exposing the immobilised biomolecule to a release agent and/or by altering the pH. The biomolecule is released from the derivatised support in an unmodified form.

The immobilised biomolecule can be stored on the derivatised support by drying the biomolecule to the support.

Accordingly, in one aspect of the present invention, there is provided a method for binding a biomolecule including at least one primary amine group, to a support, the method comprising the step of:
i) contacting a solution of the mixture with a mobile or immobilised support comprising one or more functional groups independently selected from 1,3-ketoesters, 1,3-ketothioester or 1,3-ketoamides to form a covalently bound support-biomolecule compound,
wherein the 1,3-ketoester, 1,3-ketothioester or 1,3-ketoamide is a group of Formula 1:

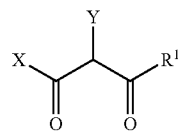

Formula 1 wherein
R¹ is an optionally substituted hydrocarbyl, perhalogenated hydrocarbyl, or a heterocyclyl group;
Y is hydrogen, an optionally substituted hydrocarbyl, or a heterocyclyl group;
X is —O, —NR² or —S, wherein the free valence of —O, —NR² or —S is bonded to the support optionally via a linker; and
R² is hydrogen, an optionally substituted hydrocarbyl, or a heterocyclyl group.

In one embodiment the method further comprises the step of washing the support-biomolecule compound.

In one embodiment the method further comprises the step of releasing the biomolecule from the support-biomolecule compound and recovering the biomolecule; and optionally recovering the support.

In one embodiment the method further comprises the steps of: carrying out one or more chemical reactions on the support-biomolecule compound to synthesise support-biomolecule-drug compound; optionally washing the support-biomolecule-drug compound; and releasing a biomolecule-drug conjugate from the support-biomolecule-drug compound, optionally, the method further comprises the step of recovering the support.

In one embodiment the method further comprises the step of drying the support-biomolecule compound; optionally, the method further comprises the step of releasing the biomolecule from the support-biomolecule compound and recovering the biomolecule.

In one embodiment, there is provided a method for purifying the biomolecule from a mixture, which further comprises the step of: (ii) washing the support-biomolecule compound. Optionally, the method further comprises the step of: (iii) releasing the biomolecule from the support-biomolecule compound and recovering the biomolecule. Further optionally, the method further comprises the step of: (iv) recovering the support.

In one embodiment, there is provided synthesising a biomolecule-drug conjugate which further comprises the step of (ii) carrying out one or more chemical reactions on the support-biomolecule compound to synthesis a support-biomolecule-drug compound. Optionally, the method further comprises the step of: (iii) washing the support-biomolecule-drug compound. Further optionally, the method comprises the step of: (iv) releasing the biomolecule-drug compound from the support-biomolecule-drug compound. Further optionally, the method further comprises the step of: (v) recovering the support.

In one embodiment, the method of step (ii) of carrying out one or more chemical reactions on the support-biomolecule compound comprises binding a drug linker to the support-biomolecule to form a support-biomolecule-drug linker compound. Optionally, the method also comprises adding a drug to the support-biomolecule-drug linker compound to form a support-biomolecule-drug linker-drug compound. Preferably, the drug linker is added to the support-biomolecule compound in a solvent. Ideally, the solvent is acetonitrile. Acetonitrile is not a hydrogen bond disrupter and therefore does not remove biomolecule from the support.

In one embodiment, there is provided a method for storing a biomolecule which further comprises the step of: (ii) drying the support-biomolecule compound. Optionally, the method further comprises the step of: (iii) releasing the biomolecule from the support-biomolecule compound and recovering the biomolecule. Further optionally, the method further comprises the step of: (iv) recovering the support.

In an embodiment the support is a bead. The beads range in size from diameters of 10 μm to 2000 μm, preferably from 50 μm to 1000 μm, and most preferably from 75 μm to 500 μm. A preferred embodiment of the support is that the bead is porous in nature with a high surface area.

A biomolecule may be a chemical compound that naturally occurs in a living organism. A biological molecule may be a derivative of a chemical compound that naturally occurs in a living organism. A derivative of a biomolecule can be a biomolecule that has been altered chemically or genetically in a way which does not affects its biological activity. A derivative is a functional derivative. A derivative is a biologically effective analogue of the parent biomolecule.

A biomolecule can be a monomer or a polymer. A biomolecule can be a micromolecule or a macromolecule. A biomolecule might have a molecular weight of at least 50 K daltons, for example, 100, 200, 300, 400, 500, 600, 700, 800, 900 or 1000 K daltons.

In an embodiment the biomolecule is selected from the group comprising: antibodies, antibody fragments, modified antibodies, antibody-drug conjugates, enzymes, proteins, peptides, polypeptides, modified peptides, peptide nucleic acids (PNAs), metalloproteins, peptide-drug conjugates, peptide-oligonucleotide hybrids, amino acids, non-naturally occurring amino acids, diamino acids, synthetic amino acids, amino acid-drug conjugates, oligonucleotides, modified oligonucleotides, oligonucleotide-drug conjugates, nucleotides, nucleosides, purines, pyrimidines, oligosaccharides, polysaccharide, disaccharides, monosaccharides, amino sugars, lipids, phospholipids, glycolipids, sterols, vitamins, hormones, steroids, neurotransmitters, carbohydrates, sugars, viruses, cells, active pharmaceutical ingredients (APIs), and precursor compounds or a derivatives of any of these. In an embodiment, the biomolecule is a vaccine, such as a virus for use in a vaccine.

In an embodiment the biomolecule is an antibody.
In an embodiment the biomolecule is an antibody fragments.
In an embodiment the biomolecule is a modified antibody.
In an embodiment the biomolecule is an antibody-drug conjugate.
In an embodiment the biomolecule is an enzyme.
In an embodiment the biomolecule is a protein.
In an embodiment the biomolecule is a peptide.
In an embodiment the biomolecule is a polypeptide.
In an embodiment the biomolecule is a modified peptide.
In an embodiment the biomolecule is a peptide nucleic acid (PNAs).
In an embodiment the biomolecule is a metalloprotein.
In an embodiment the biomolecule is a peptide-drug conjugate.
In an embodiment the biomolecule is a peptide-oligonucleotide hybrid.
In an embodiment the biomolecule is an amino acid.
In an embodiment the biomolecule is a non-naturally occurring amino acid.
In an embodiment the biomolecule is a diamino acid.
In an embodiment the biomolecule is a synthetic amino acid.
In an embodiment the biomolecule is an amino acid-drug conjugate.
In an embodiment the biomolecule is an oligonucleotide.
In an embodiment the biomolecule is a modified oligonucleotide.
In an embodiment the biomolecule is an oligonucleotide-drug conjugate.
In an embodiment the biomolecule is a nucleotide.
In an embodiment the biomolecule is a nucleoside.
In an embodiment the biomolecule is a purine.
In an embodiment the biomolecule is a pyrimidine.
In an embodiment the biomolecule is an oligosaccharide.
In an embodiment the biomolecule is a polysaccharide
In an embodiment the biomolecule is a disaccharide.
In an embodiment the biomolecule is a monosaccharide.
In an embodiment the biomolecule is an amino sugar.
In an embodiment the biomolecule is a lipid.
In an embodiment the biomolecule is a phospholipid.
In an embodiment the biomolecule is a glycolipid.
In an embodiment the biomolecule is a sterol.
In an embodiment the biomolecule is a vitamin.
In an embodiment the biomolecule is a hormone.
In an embodiment the biomolecule is a steroid.
In an embodiment the biomolecule is a neurotransmitter.
In an embodiment the biomolecule is a carbohydrate.
In an embodiment the biomolecule is a sugar.
In an embodiment the biomolecule is a virus.
In an embodiment the biomolecule is a cell.
In an embodiment the biomolecule is an active pharmaceutical ingredient (API).
In an embodiment, the biomolecule is a vaccine.
In another embodiment, the biomolecule may be selected from any two or more of the above-mentioned biomolecules.

In a further embodiment, the biomolecule may bind selectively to the derivatised support. Thus, if two or more biomolecules are actually present in the original mixture (normally there being only a single biomolecule present in the original solution together with impurities) then only one biomolecule may be actually bound depending on conditions. Alternatively, more than one may be bound. The release of a particular biomolecule may be controlled selectively by changing the release conditions and/or release agent. The pH may be adjusted so that the derivatised support preferentially binds a first biomolecule rather than a second or further biomolecule. The isoelectric point (the pI) of a biomolecule may be exploited to determine a suitable pH for the binding of a particular biomolecule and the exclusion of one or more other biomolecules. Similarly, isoelectric point of a biomolecule may be exploited to determine a suitable pH for the release of a particular biomolecule whilst one or more different biomolecules remain bound to the derivatised support.

Preferably, in any of the aforementioned or later mentioned embodiments of the invention, the biomolecule is an antibody or an antibody fragment. Ideally, the biomolecule is any of the aforementioned or later mentioned embodiments of the invention is an antibody. The antibody may be an immunoglobulin (Ig). Five human immunoglobulin classes (IgG, IgA, IgM, IgD and IgE) exist. The term antibody encompasses monoclonal antibodies. The term antibody encompasses polyclonal antibodies. The term antibody encompasses antibody fragments so long as they exhibit the desired biological activity. The antibody can be a human antibody, an animal antibody, a murine antibody, a humanised antibody or a chimeric antibody that comprises human and animal sequences.

The basic unit of the antibody structure is a heterotetrameric glycoprotein complex of at least 20,000 daltons, for example about 150,000 daltons. An antibody might be at least 900 amino acids in length, for example 1400 amino acids in length. An antibody may composed of two identical light (L) chains and two identical heavy (H) chains, linked together by both noncovalent associations and by disulfide bonds. Each heavy and light chain also has regularly spaced intrachain disulfide bridges. Each heavy chain is of about 50,000 daltons. Each heavy chain is at least 300 amino acids in length, for example about 450 amino acids in length. The antibody may be a heavy chain only antibody. Each light chain is of about 20,000 daltons. Each light chain is at least 100 amino acids in length, for example about 250 amino acids in length.

An antibody biomolecule can contain two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). In an embodiment the biomolecule is an antibody fragment. Antibody fragments comprise a portion of a full length antibody, generally the antigen binding or variable region thereof. Examples of antibody fragments include Fab, pFc' F(ab')2, and scFv fragments; diabodies; linear antibodies; single-chain antibody biomolecules; and multispecific antibodies formed from antibody fragments. An antibody fragment might be at least 10 amino acids in length, for example an antibody fragment might be at least 20, 40, 60, 80, 100, 120, 140, 160, 180, 200, 220, 240, 260, 280 or 300 amino acids in length.

In an embodiment the biomolecule is a modified antibody or a modified antibody fragment. By "modified antibody" or "modified antibody fragment" is meant an antibody that differs from a parent antibody by virtue of at least one amino acid modification. Or a modified antibody or modified antibody fragment refers to an antibody, which in comparison to the wild-type antibody, is different with respect to its size, or which is different with respect to its glycosylation but which has a similar affinity to its ligand as the wild-type antibody.

In an embodiment the biomolecule is an antibody-drug conjugate. An antibody-drug-conjugate is an antibody that is chemically bonded to a drug. An antibody fragment-drug-conjugate is an antibody fragment that is chemically bonded to a drug. A modified antibody-drug-conjugate is a modified antibody that is chemically bonded to a drug. A drug is any substance that, when administered into the body of a living organism, alters normal bodily function. A drug is a substance used in the treatment, cure, prevention, or diagnosis of disease or used to otherwise enhance physical or mental well-being.

In an embodiment the biomolecule is an enzyme. An enzyme is a protein or a protein-based molecule that can catalyse a chemical reaction. An enzyme can also be an RNA based molecule, such as a ribozyme, that can catalyse a chemical reaction. An enzyme may be a globular protein. An enzyme may be at least 20, 30, 40, 50, 60, 80 or 100 amino acids in length. An enzyme may be between 50 and 3000 amino acids in length. An enzyme may be bound to a cofactor. An enzyme may be bound to an inhibitor.

In an embodiment the biomolecule is a peptide. As used herein, by "peptide" and "protein" mean at least two covalently attached amino acids linked by a peptidyl bond. A peptide comprises amino acid residues that are linked by covalent peptide (—C(O)NH—) or thiopeptide (—C(S)NH—) bonds. The term peptide includes proteins, polypeptides and oligopeptides. A peptide may be a globular protein or a fibrous protein. The peptidyl group may comprise naturally occurring amino acids and peptide bonds, or synthetic peptidomimetic structures, i.e. "analogs", such as peptoids. The amino acids may either be naturally occurring or non-naturally occurring or synthetic; as will be appreciated by those in the art. For example, homo-phenylalanine, citrulline, and norleucine are considered amino acids for the purposes of the invention, and both D- and L- (R or S) configured amino acids may be utilized. The term "peptide" encompasses purified natural products, or products which may be produced partially or wholly using recombinant or synthetic techniques.

The terms peptide and protein encompass biomolecules comprising amino acid chains of any length but preferably of at least 20 amino acids. A peptide may be at least 20, 30, 40, 50, 60, 80 or 100 amino acids in length. A peptide may be a full-length protein.

The terms peptide and protein may refer to an aggregate of a peptide such as a dimer or other multimer, a fusion peptide, a peptide variant, or derivative thereof. The term also includes modifications of the peptide, for example, peptides modified by glycosylation, acetylation, phosphorylation, pegylation, ubiquitination, and so forth. A peptide may comprise amino acids not encoded by a nucleic acid codon.

In an embodiment the biomolecule is a modified peptide. By "modification" is meant an amino acid substitution, insertion, and/or deletion in a polypeptide sequence or an alteration to a moiety chemically linked to a protein. For example, a modification may be an altered carbohydrate or PEG structure attached to a protein.

In an embodiment the biomolecule-drug compound is a peptide-drug compound. The peptide-drug compound can be bound to the derivatised support to form a support-peptide-drug compound. A peptide-drug-compound is a peptide that is chemically bonded to a drug. A drug is any substance that, when administered into the body of a living organism, alters normal bodily function. A drug is a substance used in the treatment, cure, prevention, or diagnosis of disease or used to otherwise enhance physical or mental well-being. Preferably, the biomolecule-drug compound is an antibody-drug compound. The antibody-drug compound can be bound to the derivatised support to form an antibody-peptide-drug compound.

In an embodiment the biomolecule is an amino acid. By "amino acid" is intended to mean a moiety having an amine group and a carboxylic acid group. The amino acid residue may have one or more amine groups and one or more carboxylic acid groups. Thus the term "amino acid residue" is intended to include both natural and synthetic amino acids. The class of natural amino acids includes both proteinogenic amino acids and also naturally occurring non-proteinogenic amino acids. These naturally occurring non-proteinogenic amino acids are those that may be found, for example, in the body or in food stuffs, but which do not participate in protein biosynthesis. There are twenty-two proteinogenic amino acids and of the twenty-two, only twenty are directly encoded by the universal genetic code.

The remaining two, selenocysteine and pyrrolysine, are incorporated into proteins by unique synthetic mechanisms. The invention is intended to encompass the twenty universally encoded amino acids plus the remaining two mentioned above. The term "amino acid residue" is therefore intended to include the following: Alanine, Cysteine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, Tyrosine, Selenocysteine and Pyrrolysine.

In addition to amino acid having a terminal carboxylic acid or amine group, the term is also intended to include: an amino acid alkyl ester (e.g. an amino acid $C_{1-6}$ alkyl ester); an amino acid aryl ester; an N-alkylated amino acid (e.g. a $C_{1-6}$ N-alkylated amino acid such as N-methylated amino acid or an N-methylcyclopropylated amino acid); an N,N-dialkylated amino acid (e.g. a $C_{1-6}$ N,N-dialkylated amino acid, which can include N,N-dimethylcyclopropylated amino acids), preferably the N,N-dialkylated amino acid is an N,N-dimethylated amino acid; an N-acylated amino acid (e.g. a $C_{1-6}$ N-acylated amino acid); an N-arylated amino acid; an N-alkylated amino acid ester; an N-acylated amino acid ester; an N-arylated amino acid ester; an O-alkylated amino acid (e.g. a $C_{1-6}$ O-alkylated amino acid); an O-arylated amino acid; an O-acylated amino acid; an O-alkylated amino acid ester; an O-arylated amino acid ester; an O-acylated amino acid ester; an S-alkylated amino acid; an S-acylated amino acid; an S-arylated amino acid; an S-alkylated amino acid ester; an S-acylated amino acid ester; or an S-arylated amino acid ester. In other words, the invention also envisages amino acid derivatives such as those mentioned above which have been functionalized by simple synthetic transformations known in the art (e.g. as described in "Protective Groups in Organic Synthesis" by TW Greene and PGM Wuts, John Wiley & Sons Inc (1999), and references therein. Of course, in N,N-dialkylated amino acids, the alkyl groups may be the same or different.

In addition, the side chains of the above amino acids can be in either the (R) or the (S) configuration. In other words, both L- and D-amino acids are within the scope of the present invention, though the D-amino acids are of course not naturally occurring.

The term "amino acid" also includes non-proteinogenic amino acids such as amino acids which can be incorporated into proteins during translation (including pyrrolysine, ornithine and selenocysteine). The term "non-proteinogenic amino acid" also includes homologues of proteinogenic amino acids such as, but not limited to, homoarginine. The term "non-proteinogenic amino acid" also includes beta amino acids such as, but not limited to, beta Alanine. The term "amino acid" also includes lactam analogues of natural amino acids such as, but not limited to, pyroglutamine.

In an embodiment the biomolecule is a non-naturally occurring amino acid. A non-naturally occurring amino acid is an organic compound which is an amino acid, but is not among those encoded by the standard genetic code, or incorporated into proteins during translation. Non-proteinogenic amino acids, thus, include amino acids or analogues of amino acids other than the 20 proteinogenic amino acids and include, but are not limited to, the D-isostereomers of proteinogenic amino acids. Examples of non-proteinogenic amino acids include, but are not limited to: citrulline, homocitrulline, hydroxyproline, homoarginine, homoserine, homotyrosine, homoproline, ornithine, 4-amino-phenylalanine, sarcosine, biphenylalanine, homophenylalanine, 4-nitro-phenylalanine, 4-fluoro-phenylalanine, 2,3,4,5,6-pentafluoro-phenylalanine, norleucine, cyclohexylalanine, N-acetic acid, O-methyl serine, α-aminoisobutyric acid, N-methyl-alanine, N-methyl-glycine, N-methyl-glutamic acid, tert-butylglycine, α-aminobutyric acid, α-aminoisobutyric acid, acedic acid, 2-aminoisobutyric acid, 2-aminoindane-2-carboxylic acid, selenomethionine, lanthionine, dehydroalanine, γ-amino butyric acid, naphthylalanine, aminohexanoic acid, phenylglycine, pipecolic acid, 2,3-diaminoproprionic acid, tetrahydroisoquinoline-3-carboxylic acid, tert-leucine, tert-butylalanine, cyclohexylglycine, diethylglycine, dipropylglycine and derivatives thereof wherein the amine nitrogen has been mono- or di-alkylated. Other examples of non-proteinogenic amino acids include para amino benzoic acid (PABA), 5-amino salicylic acid (5-ASA) and 4-amino salicylic acid (4-ASA), Aib (aminobutyric acid), bAib (3-aminoisobutyric acid), Nva (norvaline), [beta]-Ala, Aad (2-aminoadipic acid), bAad (3-aminoadipic acid), Abu (2-aminobutyric acid), Gaba ([gamma]-aminobutyric acid), Acp (6-aminocaproic acid), Dbu (2,4-diaminobutyric acid), [alpha]-aminopimelic acid, TMSA (trimethylsilyl-Ala), alle(allo-isoleucine), Nle (norleucine), tert-Leu, Cit (citrulline), Orn, Dpm (2,2'-diaminopimelic acid), Dpr (2,3-diaminopropionic acid), [alpha]- or [beta]-NaI, Cha (cyclohexyl-Ala), hydroxyproline, Sar (sarcosine), etc.; cyclic amino acids; N-[alpha]-alkylated amino acids, e.g., MeGly (N-[alpha]-methylglycine), EtGly (N-[alpha]-ethylglycine), and EtAsn(N-[alpha]-ethylasparagine); and amino acids with two side chain substituents at the [alpha]-carbon, etc. Further examples of non-proteinogenic amino acids include dolaproine (Dap), dolaisoleuine (Dil), dolaphenine (Doe) and dolavaline (Dov); and unusual amino acids derived from natural sources.

In an embodiment the biomolecule is a synthetic amino acid. A synthetic amino acid is an amino acid that has been made synthetically. A synthetic amino acid is an amino acid that has not been synthesised within a living system. Examples of synthetic amino acids include nitro-phenylalanine and nitro-tyrosine.

In an embodiment the biomolecule is an amino acid-drug conjugate. An amino acid-drug-conjugate is an amino acid that is chemically bonded to a drug. A drug is any substance that, when administered into the body of a living organism, alters normal bodily function. A drug is a substance used in the treatment, cure, prevention, or diagnosis of disease or used to otherwise enhance physical or mental well-being.

In an embodiment the biomolecule is an oligonucleotide. The term "oligonucleotide" includes linear oligomers of nucleosides or analogs thereof, including deoxyribonucleosides, ribonucleosides, and the like. Usually oligonucleotides range in size from a few monomeric units, e.g. 2-4, to several hundreds of monomeric units. For example, an oligonucleotide may be at least 10, 50, 100, 150, 200, 400, 600, 800, 1000, or 2000 nucleotides in length. Oligonucleotides can be obtained from existing nucleic acid sources, including genomic or cDNA, or can be produced by synthetic methods. The nucleotide residues can be coupled to each other by any of the numerous known internucleoside linkages. Such internucleotide linkages include, without limitation, phosphodiester, phosphorothioate, phosphorodithioate, methylphosphonate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages.

In an embodiment the biomolecule is a modified oligonucleotide. The term "modified oligonucleotide" encompasses an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. The term "modified oligonucleotide" also encompasses oligonucleotides having at least one nucleotide with a modified base and/or sugar, such as a 2'-O-substituted, a 5'-O-substituted and/or a 3'-O-substituted ribonucleotide. The term "modified oligonucleotide" also encompasses oligonucleotides having at least one substitution, insertion, and/or deletion of a base.

In an embodiment the biomolecule is an oligonucleotides-drug conjugate. An oligonucleotide-drug-conjugate is an oligonucleotide that is chemically bonded to a drug. A drug is any substance that, when administered into the body of a living organism, alters normal bodily function. A drug is a substance used in the treatment, cure, prevention, or diagnosis of disease or used to otherwise enhance physical or mental well-being.

In an embodiment the biomolecule is a nucleotide. The term "nucleotide" generally refers to a nucleoside comprising a phosphorous-containing group attached to a sugar, usually ribose or deoxyribose.

In an embodiment the biomolecule is a nucleoside. A nucleoside generally refers to compounds consisting of a sugar, usually ribose or deoxyribose, and a purine or pyrimidine base.

In an embodiment the biomolecule is a purine. A purine is a nitrogenous base. A purine is a heterocyclic, aromatic organic compound consisting of a pyrimidine ring fused to an imidazole ring. Purines, include substituted purines and their tautomers.

In an embodiment the biomolecule is a pyrimidine. A pyrimidine is a single-ringed, crystalline organic base, $C_4H_4N_2$, that forms uracil, cytosine, or thymine In an embodiment the biomolecule is an oligosaccharide. Oligosaccharides are compounds comprising 2 to 10 monosaccharide residues.

In an embodiment the biomolecule is a polysaccharide. A polysaccharide is a polymer of monosaccharides containing 10 or more monosaccharide residues. For example a polysaccharide may comprise at least 10, 30, 50, 100, 500 or 1000 monosaccharide residues.

In an embodiment the biomolecule is a monosaccharide. A monosaccharide is a carbohydrate, such as a tetrose, pentose, or a hexose, that cannot be broken down to simpler sugars by hydrolysis. The term "monosaccharide" is intended to also cover derivatives of monosaccharides and oligosaccharides, in particular the reduced and oxidised forms thereof, such as sugar alcohols, e.g. sorbitol, mannitol, lactitol.

In an embodiment the biomolecule is an amino sugar. An amino sugar is a derivative of a sugar that contains an amine group in place of a hydroxyl group.

In an embodiment the biomolecule is a precursor compound. A precursor compound is a compound that participates in the chemical reaction that produces a biomolecule. A precursor compound may an intermediate compound in a chain of chemical reactions, from which a biomolecule is produced. A precursor compound may be a substance from which a more mature biomolecule is formed.

In an embodiment the biomolecule is a derivative of a biomolecule. The term derivative can mean a biological molecule that has been altered chemically or genetically in a way which does not affects its biological activity. A derivative is a functional derivative. A derivative is a biologically effective analogue of the parent biomolecule.

A biomolecule-drug conjugate is a species in which the biomolecule is covalently bonded to a drug molecule. A drug is any substance that, when administered into the body of a living organism, alters normal bodily function. A drug is a substance used in the treatment, cure, prevention, or diagnosis of disease or used to otherwise enhance physical or mental well-being. The present invention includes any drug currently approved by the FDA at Dec. 31, 2010. For example, biomolecule-drug conjugates include: ReoPro; Humira; Campath; Simulect; Avastin; Erbitux; Cimzia; Zenapax; Soliris; Raptiva; Mylotarg; Zevalin; Remicade; Orthoclone OKT3; Tysabri; Xolair; Synagis; Vectibix; Lucentis; Rituxan, Mabthera; Bexxar; Herceptin.

In an embodiment, the step of contacting the biomolecule with the support comprises incubating the biomolecule with the support. The incubation may be carried out between 0 and 100° C., preferably between 5 and 50° C. and optionally between 10 and 40° C. Ideally, the incubation is carried out between 15 and 37° C., e.g. the incubation is carried out at room temperature, such as 21° C. Alternatively, the incubation is carried out at 37° C. At 37° C. the kinetics of the binding reaction are improved. The incubation may be carried out for between 1 minute and 3 days. Preferably the incubation is carried out at between 20 minutes and 1 hour. Incubation may be carried out in an aqueous media. Alternatively, the aqueous media comprises a co-solvent. The co-solvent may be present within a range of 0.5-50% v/v. In a preferred embodiment, the incubation is carried out at an acidic pH, such as between pH6-7, ideally at pH 6.5. This results in improved binding of the antibody to the derivatised support.

In an embodiment the step of releasing the biomolecule from the support is selected from:

a) exposing the support-biomolecule compound to a release agent; and b) altering the pH to break the support-biomolecule bond.

In an embodiment the release agent is a primary amine which may be any compound comprising a primary amine group. Preferably the compound is a small molecule. The primary amine comprising compound can displace the biomolecule from the support by forming a covalent bond with the support.

In an embodiment the primary amine is selected from the group comprising, but not limited to: hydrazine, hydroxylamine, lysine, arginine, histidine and ethanolamine. In one embodiment, the release agent is hydrazine. Advantageously, the use of hydrazine results in effective release of the biomolecule from the support. In an alternative embodiment, the release agent is selected from lysine, arginine and histidine. Advantageously, these release agents are non-toxic. In one preferred embodiment, the release agent is non-toxic. Ideally the reagent in a GRAS (generally regarded as safe) reagent as recognised by regulatory authorities such as the FDA. In a further embodiment, the release agent is selected from guanidine, ammonia, $NH_4OH$ (preferably 0.1M $NH_4OH$ in PBS at pH10), 2-Amino-2-hydroxymethyl-propane-1,3-diol (TRIS) (preferably 0.1M TRIS in PBS at pH10), NaOH (preferably 0.1M NaOH in PBS at pH10). In a further embodiment, the release agent is a hydrogen bond disrupter such as co-solvents of Hexafluoroisopropanol, 2,2,2-Trifluoroethanol or dimethylsulfoxide (DMSO).

In an embodiment the release agent is a nucleophile which may be a compound or functional group that is attractive to centres of positive charge, and donates electrons, especially donating an electron pair to an electrophile to form a bond. The nucleophile can displace the biomolecule from the derivatised support by forming a covalent bond with the derivatised support. The nucleophile can be selected from the group comprising: hydroxylamine and ammonia. In one embodiment, the cleavage reagent comprises a primary amine. Preferably, the primary amine is suitable for carrying out nucleophilic displacement of the biomolecule from the derivatised support.

In an embodiment, the release agent is incubated with the support-biomolecule. The incubation may be carried out between 0 and 100° C., preferably between 5 and 50° C. and optionally between 10 and 40° C. Ideally the incubation is carried out between 15 and 37° C., e.g. the incubation is carried out at room temperature, such as 21° C. Alternatively, the incubation is carried out at 37° C. At 37° C. the kinetics of the release reaction are improved. The incubation may be carried out for between 1 minute and 3 days. Preferably the incubation is carried out at between 30 minutes and 2 hours. Incubation is carried out in an aqueous media.

The pH can be altered by any amount that is sufficient to break the support-biomolecule bond but which will not affect the activity, integrity or 3D structure of the biomolecule, for example, the pH can be adjusted so that it is basic. In an embodiment the pH is increased to being greater than pH 8. For example, the pH can be increased to about pH9. The pH can be increased to being greater than pH9. For example, the pH can be increased to about pH10. The pH can be increased to being greater than pH10, but usually will be less than pH14.

In an embodiment, a release agent is used and the pH is adjusted to basic. In an embodiment, the pH is adjusted to between 7 and 14, such as between 7 and 12. Less than pH 12 is preferably for biomolecules, however, biomolecules are expected to be able to withstand short incubations, such as for less than 5 minutes, at pH 14. Typically, the pH is adjusted to between 9 and 11. For example, the pH of the following release agents can be adjusted to achieve effect release of the biomolecule from the support:

Hydrazine at pH 9-11
Arginine at pH 9-11
Lysine at pH 9-11
Histidine at pH 9-11

The support-biomolecule compound may undergo one or more treatments with release agent. Advantageously, the use of a second or subsequent treatment with fresh release agent may result in increasing the amount of biomolecule released from the derivatised support. Fresh release agent is release agent that has not previously been incubated with the biomolecule-support compound.

In an embodiment the step of washing the support-biomolecule compound comprises removing substances that are not covalently bound to the support or biomolecule such as contaminants. Typical contaminants include proteins, viruses, lipids, cells debris. Any medium that does not affect the activity, integrity or 3D structure of the biomolecule or the integrity of the support-biomolecule bond can be used to wash the support-biomolecule.

Preferably the buffer is isotonic and induces a stable environment to biomolecules such as antibodies by mimicking physiological pH and ionic strength. In an embodiment, the biomolecule support is washed by filtration. Optionally, the resultant filtrate is buffer-exchanged, e.g. by centrifugation using membrane cartridges.

Typically, additives are introduced to the buffer media. These additives induce a level of control to the buffer system and the biomolecule contained within it. For example, additives such as Tris or histidine are introduced to a buffered process stream to maintain pH and minimise incidental acidification through lysosomal disruption. Typically, the pH of a biomolecule process stream should be maintained between pH 3 and 9.5, with the extremes of the pH limits avoided for prolonged periods. Inorganic salts such as 0.1 M NaCl(aq) may be added to maintain the ionic strength of the process stream. Ionic & non-ionic detergents such as Tween (polysorbate) may be added to the buffer to favourably increase the solubility of poorly soluble biomolecules in the buffer media and minimise aggregation. However, as the detergents bind tightly to the biomolecules their removal can be troublesome.

Prior to binding the biomolecule to the derivatised support, the biomolecule may be desalted, for example, by using a desalt column, such as a PD10 column containing Sephadex™ G-25 packing material (GE Healthcare, 1.45×5.0 cm (8.3 ml) packed bed dimensions).

Alternatively, the addition of 9M urea or 6M guanidine hydrochloride solutions may be added to infer an identical solubilisation effect but these reagents must also be used with care. Urea and guanidine hydrochloride are known to denature and de-stabilise biomolecules such as proteins and antibodies. Denaturation may lead to aggregation of the desired biomolecule.

Chelating agents such as EDTA are typically utilised in biomolecule processing for the removal of divalent metal species. The addition of a chelating additive to remove these co-contaminants reduces the oxidation potential of the biomolecule and avoids denaturation through β-elimination. Similarly, stabilisers such as disaccharides (e.g. Trehalose) and glycerol are commonly added to antibody process streams to minimise protein-protein interactions and thus aggregation.

For biomolecules which have been stored for prolonged periods the buffer media may also include a preservative (e.g. ProClin™, Sodium azide, Thimersal, etc.). Additives serve to protect the biomolecule from oxidation and minimise microbial contamination. Another means of preventing oxidation is the addition of reducing agents such as 1,4-dithiothreitol. The addition of reducing agents must also be undertaken with great care to avoid disruption of the tertiary structure of the biomolecule through reduction of disulphide bridges.

The presence of Protease Inhibitors (e.g. phenylmethylsulfonyl fluoride) is also commonplace within the extraction process of proteins. These additives serve to protect the protein from digestion by proteases which are released when cellular structures are disrupted during the extraction process.

In an embodiment the support-biomolecule compound is washed with a buffer, optionally wherein the buffer is phosphate buffered saline (PBS). Any buffer that does not affect the activity, integrity or 3D structure of the biomolecule or the integrity of the support-biomolecule bond can be used to wash the support-biomolecule. Suitable buffers include:

Potassium phosphate buffer;
Sodium phosphate buffer;
Sodium citrate buffer;
Bis-Tris propane buffer;
HEPES buffer;
Sodium acetate buffer;
Sodium citrate buffer;
Cacodylic acid buffer;
Ammonium acetate buffer;
Imidazole buffer;
Bicine buffer;
2-(N-morpholino)ethanesulfonic acid (MES) buffer.

Recovery of a protein from a support can be assessed using a quantitative Bradford assay and A280 UV spectrometry (such as described in Voet. (1999). Proteins, primary structure. In: *Fundamentals of Biochemistry*. USA: Wiley. page 100). A280 means an absorption maxima of 280 nm. The skilled person will appreciate that proteins in solution absorb ultraviolet light with absorbance maxima at 280 and 200 nm. Amino acids with aromatic rings are the primary reason for the absorbance peak at 280 nm. Peptide bonds are primarily responsible for the peak at 200 nm. The relationship of absorbance to protein concentration is linear and thus absorbance can be used to assay the concentration of protein.

The structural integrity of a protein can be assessed using gel electrophoresis, e.g. by running the protein on a reducing or a non-reducing gel. The protein band sizes can be correlated to a stock of protein that has not been processed by a method of the present invention.

The term "purified" or "in purified form" for a biomolecule refers to the physical state of the biomolecule after being isolated from a mixture (e.g. from a reaction mixture). Thus, the term "purified" or "in purified form" for a biomolecule refers to the physical state of the biomolecule after being obtained from a purification process or processes described herein in sufficient purity to be characterizable by standard analytical techniques well known to the skilled person.

A biomolecule can be purified from a mixture using the methods and compositions of the present invention. A mixture is a material system made up by two or more different substances which are mixed together but are not combined chemically. Mixtures are the product of mixing of substances without chemical bonding or other chemical change. In an embodiment the mixture is selected from the group comprising: a process medium containing unwanted reagents and/or by-products; a chemical reaction medium containing unwanted reagents and/or by-products; and a buffer containing unwanted reagents and/or by-products.

A solution can be an aqueous solution or an organic solution. Solutions that are envisaged by the inventions are ones that do not interfere with an enamine bond or the integrity or activity of the biomolecule. Typically the solution will be an aqueous buffer maintained at a pH suitable for the structural integrity of the biomolecule (pH 3-9.5). The addition of a co-solvent (e.g. dimethylsulfoxide, DMSO) may be appropriate to enhance biomolecule or drug solubility. In one embodiment the solvent is acetonitrile. Use of acetonitrile results in an improved yield as compared to use of DMSO. This may be because DMSO is a hydrogen bond disrupter and therefore removed biomolecule from the support. Overall, the solution should infer that the activity of the biomolecule is maintained. The solution may comprise of the following additives: Buffer salts, detergents, disaccharide stabilisers, preservatives.

The 1,3-ketoester, 1,3-ketothioester or 1,3-ketoamide is a group of Formula 1:

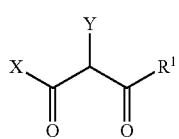

Formula 1 wherein $R^1$ is an optionally substituted hydrocarbyl, perhalogenated hydrocarbyl, or a heterocyclyl group;

Y is hydrogen, an optionally substituted hydrocarbyl, or a heterocyclyl group;

X is —O, —$NR^2$ or —S, wherein the free valence of —O, —$NR^2$ or —S is bonded to the support via an optional linker; and $R^2$ is hydrogen, an optionally substituted hydrocarbyl, or a heterocyclyl group.

In one embodiment, the support is derivatised with a 1,3-ketoester. In an alternative embodiment, the support is derivatised with a 1,3-ketothioester. In further alternative embodiment, the support is derivatised with a 1,3-ketoamide.

Hydrocarbyl groups are groups containing only carbon and hydrogen atoms, though as discussed below, the hydrocarbyl groups themselves may be optionally substituted by from one to five independently selected groups which may contain other atoms in place of or in addition to carbon and hydrogen. Hydrocarbyl groups which may be represented by $R^1$ Y, and $R^2$ include alkyl, alkenyl and aryl groups, and any combination thereof, such as aralkyl and alkaryl, for example benzyl groups.

Alkyl groups which may be represented independently by $R^1$ Y, and $R^2$ include linear and branched alkyl groups comprising from 1 to 20 carbon atoms, particularly from 1 to 8 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, i.e. cycloalkyl groups such as $C_{3-20}$ cycloalkyl, commonly comprising from 3 to 10 carbon atoms in the largest ring and optionally featuring one or more bridging rings. Examples of alkyl groups which may be represented $R^1$ Y, and $R^2$ include methyl, ethyl, propyl, 2-propyl, butyl, 2-butyl, t-butyl and cyclohexyl groups.

Alkenyl groups which may be represented by $R^1$ Y, and $R^2$ include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups.

Aryl groups which may be represented independently by $R^1$ Y, and $R^2$ may contain 1 ring or 2 or more fused rings which may also include cycloalkyl, aryl or heterocyclic rings. Examples of aryl groups which may be represented by $R^1$ Y, and $R^2$ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by $R^1$ independently include perhalogenated alkyl and aryl groups, and any combination thereof, such as aralkyl and alkaryl groups. Examples of perhalogenated alkyl groups which may be represented by $R^1$ include —$CF_3$ and —$C_2F_5$.

Heterocyclic groups which may be represented by $R^1$ Y, and $R^2$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. Examples of heterocyclic groups which may be represented by $R^1$ Y, and $R^2$ include pyridyl, pyrimidyl, pyrrolyl, thiophenyl, furanyl, indolyl, quinolyl, isoquinolyl, imidazoyl and triazoyl groups.

When any of $R^1$ Y, and $R^2$ is a substituted hydrocarbyl or heterocyclic group, the substituent(s) should be such so as not to adversely affect the rate or selectivity of the reaction. Optional substituents include halogen, cyano, nitro, hydroxy, amino, thiol, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for $R^1$ and $R^2$ above.

One to six substituents may be present and are selected independently.

$R^1$ is preferably a $C_{1-4}$ alkyl group, most preferably a methyl group.

Y is preferably hydrogen.

$R^2$ is preferably hydrogen or a $C_{1-4}$ alkyl group. When $R^2$ is a $C_{1-4}$ alkyl group, preferably $R^2$ is a methyl group. Most preferably $R^2$ is hydrogen.

In an embodiment X is —O.

In an alternative embodiment X is —$NR^2$, preferably X is —NH.

In an alternative embodiment X is —S.

In an embodiment the functional group is a 1,3-ketoamide of Formula I. In this embodiment the support comprises a 1,3-ketoamide and does not comprise a 1,3-ketoester group or a 1,3-ketothioester.

In an embodiment the functional group is a 1,3-ketoester of Formula I. In this embodiment the support comprises a 1,3-ketoester group and does not comprise a 1,3-ketoamide or a 1,3-ketothioester.

In an embodiment the functional group is a 1,3-ketothioester of Formula I. In this embodiment the support comprises a 1,3-ketothioester group and does not comprise a 1,3-ketoamide or a 1,3-ketoester.

The supports employed in the process of the present invention are derivatised with 1,3-ketoester and/or 1,3-ketothioester and/or 1,3-ketoamide pendant groups attached either directly to a polymer support or attached to a polymer support through a linking group. Linking groups include optionally substituted methylene, polymethylene, ether, polyether or cyclic bridging units.

Methylene and polymethylene bridging units include linear and branched alkylene chains comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. Examples of alkylene chains include —$CH_2$—, —$CH_2CH_2$—, —$(CH_2)_3$—, —$CH_2CH(CH_3)$—, and —$CH_2C(CH_3)_2$— chains.

Ether and polyether bridging units include linear and branched alkylene-oxy-alkylene chains or poly (alkylene-oxy)-alkylene chains comprising up to 150 carbon atoms and up to 40 oxygen atoms, particularly from 2 to 15 carbon atoms and from 1 to 4 oxygen atoms, and preferably from 2 to 6 carbon atoms and from 1 to 2 oxygen atoms.

Cyclic bridging units include aromatic, saturated and partially unsaturated ring systems and may constitute 1 ring or 2 or more fused rings which may include cycloalkyl, aryl or heterocyclic rings. In certain embodiments, cycloalkyl and aryl rings commonly comprise from 3 to 10 carbon atoms in the largest ring, and heterocyclic rings commonly comprise from 3 to 7 ring atoms in which at least one atom is carbon and at least one atom is any of N, O, S or P. Examples of aromatic, saturated and partially unsaturated ring systems which may be represented by L include —$CH_2C_6H_4CH_2$— and —$CH_2C_6H_{10}CH_2$—.

Any suitable linking group known in the art may be used in the performance of this invention. Examples of suitable linking groups may be found in Chan & White, *Fmoc Solid-Phase Peptide Synthesis*, Oxford University Press, 2000, on pages 15 to 19 inclusive and page 20 and the groups disclosed therein specifically form part of the disclosure of the present invention.

In an embodiment the covalent bond between the support and the biomolecule is an enamine bond. Primary amine groups of biomolecules are immobilised onto the support through the formation of an enamine chemical bond. The enamine bond is stabilised through hydrogen bonding. Stabilisation through hydrogen bonding is proposed to be the basis of functional selectivity of the 1,3-ketoester, 1,3-ketothioester or 1,3-ketoamide for primary amines.

In an embodiment the support is a mobile support. Suitable mobile supports include:
Polystyrene
Polystyrene (PS-DVB)—Lightly cross-linked with divinylbenzene (0.1-5.0% DVB, termed Microporous)
Polystyrene (PS-DVB)—Highly cross-linked with divinylbenzene (5-60% DVB, termed Macroporous)
Polyethylene glycol
Polyethylene glycol grafted polystyrene (PS-PEG copolymer)
Poly acrylamide
Controlled Pore Glass (CPG) beads
Silica
Kieselguhr
Polypropylene
Poly(tetrafluoroethylene)
Polyethylene
Cellulose
Poly methacrylate
Functionalised Monoliths
Functionalised Fibres
Monolithic columns (such as Nikzad et al, OPRD, 2007, 11, 458-462)
Agarose
Sepharose
Magnetic recoverable polymer beads Of these, polyethylene glycol, silica and polystyrene are particularly preferred. Polyethylene glycol and silica are most preferred.

Suitable commercial mobile supports include:
Davisil LC1000 Å (OH, irregular shaped silica)
MS-Gel D-50-1000 Å (OH, spherical, porous, high purity silica)
QuadraPure BZA ($NH_2$, macroporous PS-20% DVB)
Hydroxymethyl PS(OH, microporous PS-1% DVB)
Aminomethyl PS($NH_2$, microporous PS-1% DVB)
NovaSyn TentaGel ($NH_2$, grafted PEG-PS)
Suitable immobilised supports include:
Stents
Subcutaneous implants
Cotton
Multipin/Rod microtitre plates (such as Geysen et al, J. Immunological Methods, 1987, 102, 259

According to a second aspect, the present invention provides a support comprising:
a) a polymer such as polyether or silica; and
b) groups selected from 1,3-ketoesters, 1,3-ketothioesters or 1,3-ketoamides, of Formula I as defined above, or mixtures thereof attached to the polymer.

In an embodiment the polyether is selected from the group consisting of polyethylene glycol and $C_{1-6}$ alkoxy polyethylene glycol.

In an embodiment the support is a bead with a diameter of 10 μm to 2000 μm.

According to a third aspect, the present invention provides a support-biomolecule compound comprising:
a) a biomolecule including at least one primary amine group; and
b) a support comprising one or more functional groups independently selected from 1,3-ketoesters, 1,3-ketothioesters or 1,3-ketoamides of Formula I as defined above,
wherein the biomolecule and support form a covalently bound support-biomolecule compound. Preferably the support comprises polyether or silica.

The preferred features described previously as embodiments of the 1$^{st}$ aspect of the invention also represent preferred features for the 4$^{th}$ and 5$^{th}$ aspects of the invention.

For example in one embodiment the support is a bead with a diameter of 10 μm to 2000 μm.

Similarly for example in an embodiment the biomolecule is selected from the group comprising: antibodies, antibody fragments, modified antibodies, antibody-drug conjugates, enzymes, proteins, peptides, polypeptides, modified peptides, peptide nucleic acids (PNAs), metalloproteins, peptide-drug conjugates, peptide-oligonucleotide hybrids, amino acids, non-naturally occurring amino acids, diamino acids, synthetic amino acids, amino acid-drug conjugates, oligonucleotides, modified oligonucleotides, oligonucleotides-drug conjugates, nucleotides, nucleosides, purines, pyrimidines, oligosaccharides, polysaccharide, disaccharides, monosaccharides, amino sugars, lipids, phospholipids, glycolipids, sterols, vitamins, hormones, steroids, neurotransmitters, carbohydrates, sugars, viruses, cells active pharmaceutical ingredients (APIs), and precursor compounds or a derivatives of any of these. In an embodiment, the biomolecule is a vaccine, such as a virus for use in a vaccine.

DESCRIPTION OF THE FIGURES

Embodiments of the invention are further described hereinafter with reference to the accompanying drawings, in which.

Figure 1:
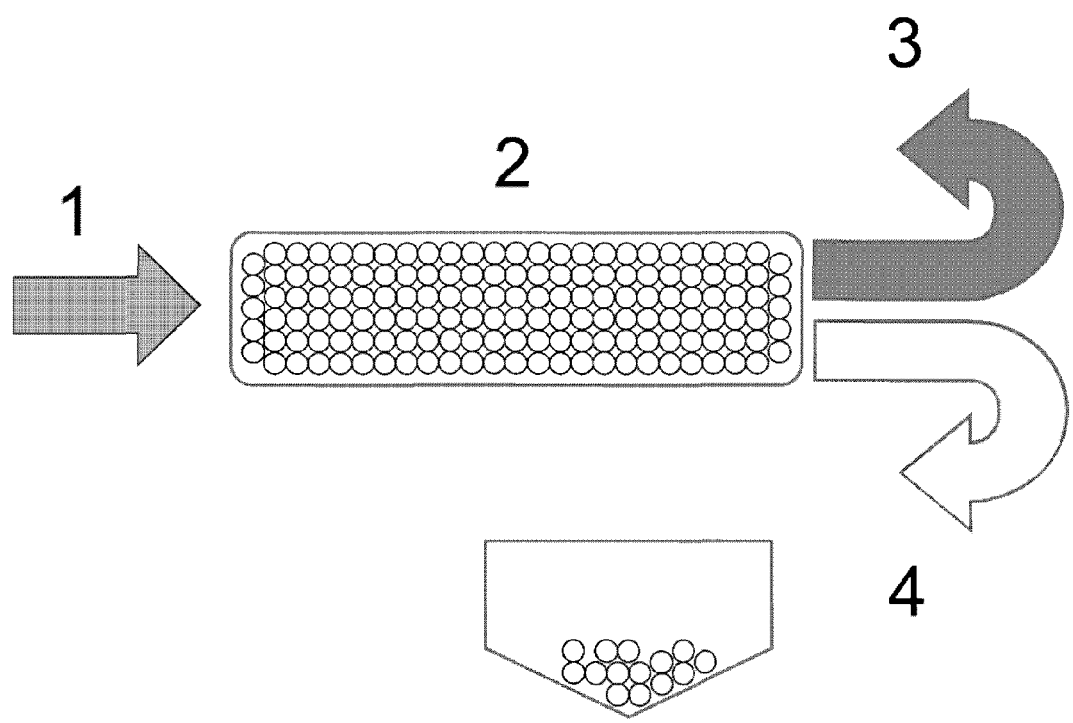
FIG. 1 is a cartoon representation of a 'lock-release' process envisaged by the invention. Antibodies are covalently bound to solid beads to form bead-antibody molecules. The bead-antibody molecules are then processed in a fixed bed or column. Process reagents are added to the bead-antibody molecules which modify the antibody. Unwanted reagents, by-products and waste are washed away leaving the bead-antibody molecules behind. The antibody is then released from the bead by a chemical key, for example hydrazine.
Figure 2:
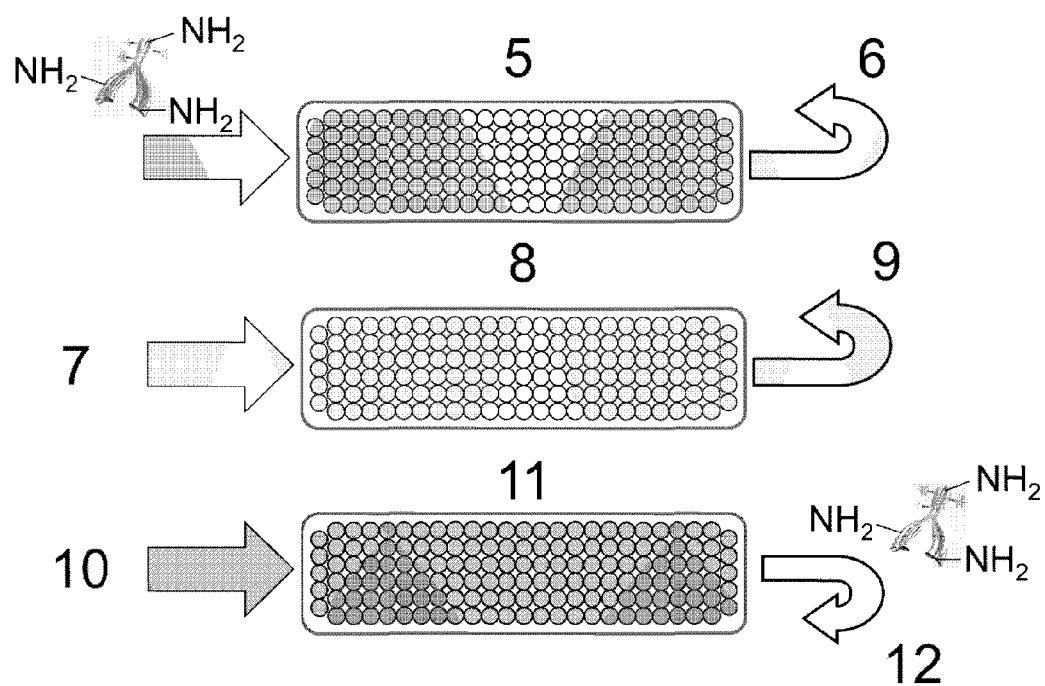

Key to FIG. 1:
1 Reagents
2 Antibody bind to beads
3 Waste disposal
4 Release to give clean Antibody product FIG. 2 a cartoon representation of a 'lock-release' process envisaged by the invention. Support beads selectively bind to antibodies through a chemical bond, e.g. a covalent bond to immobilise the antibody to the bead. Washing agent such as a buffer is flushed through the system. Excess reagents, and/or by-products are removed by washing and waste is disposed of. A release reagent is added which cleaves the antibody from the beads. Purified antibody is released.

Figure 3:
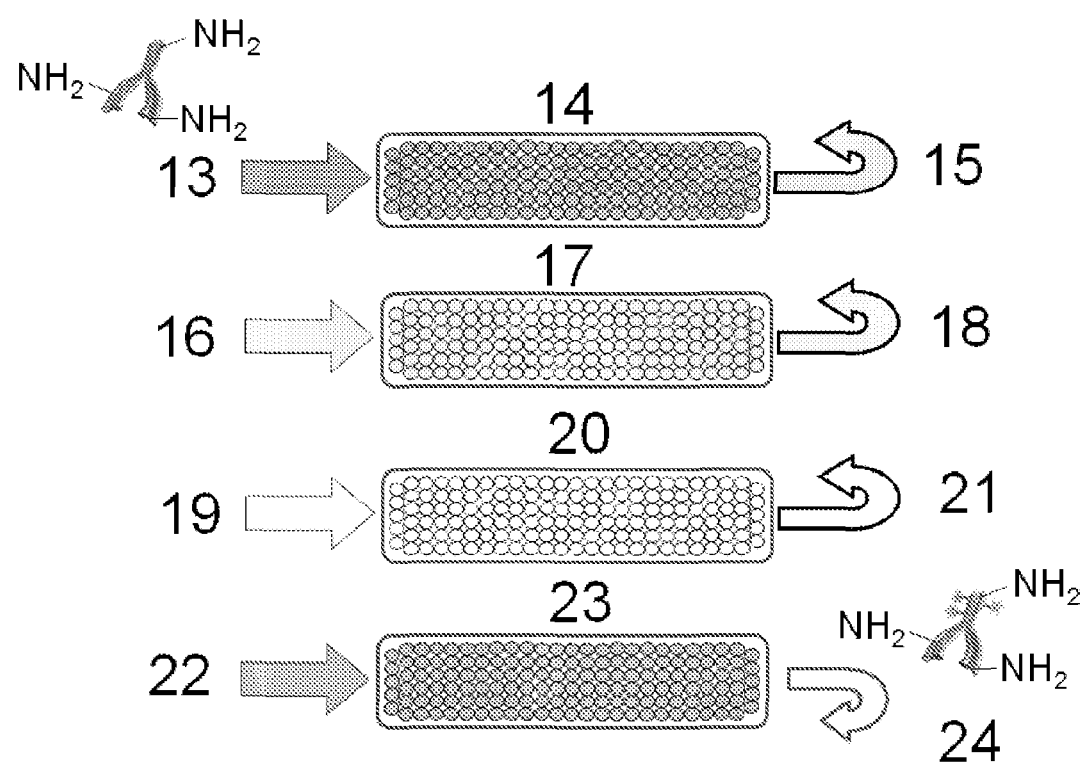

Key to FIG. 2:
5 Selective Antibody binding to beads
6 Waste Disposal
7 Flush
8 Antibody bound to beads—excess reagents removed
9 Waste disposal
10 Release Reagent
11 Cleaves Antibody bound to beads
12 Purified Antibody FIG. 3 is a cartoon representation of a 'lock-release' process envisaged by the invention. Primary amine groups in an antibody selectively bind to a support bead and unwanted reagents are removed. The antibody is immobilised on the bead and processed during one or more chemical reactions to form an antibody-drug conjugate which is retained on the bead. The immobilised antibody-drug conjugate is washed to remove waste. A release reagent is added which cleaves the antibody-drug conjugate from the bead. Purified antibody-drug conjugate is released.

Figure 4:
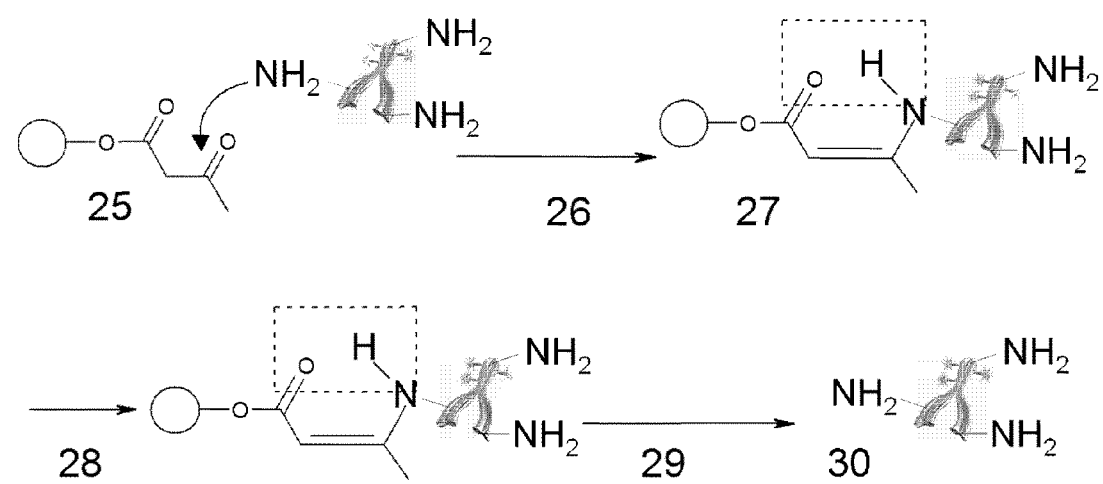

Key to FIG. 3:
13 MAb
14 Antibody binding to beads
15 Waste disposal
16 Processing of antibody
17 Modified Ab bound to beads
18 Waste disposal
19 ADC
20 Cyto binds to immobilised Ab to form immobilised ADC
21 Waste disposal
22 Release Reagent
23 Cleaves ADC from beads
24 Purified ADC FIG. 4 shows the formation of an enamine bond between a primary amine of a biomolecule and 1,3-ketoester that is comprised on the support. The enamine bond is stabilised through hydrogen bonding. The 1,3-ketoester will only react with primary amine groups on a biomolecule.

Figure 5:
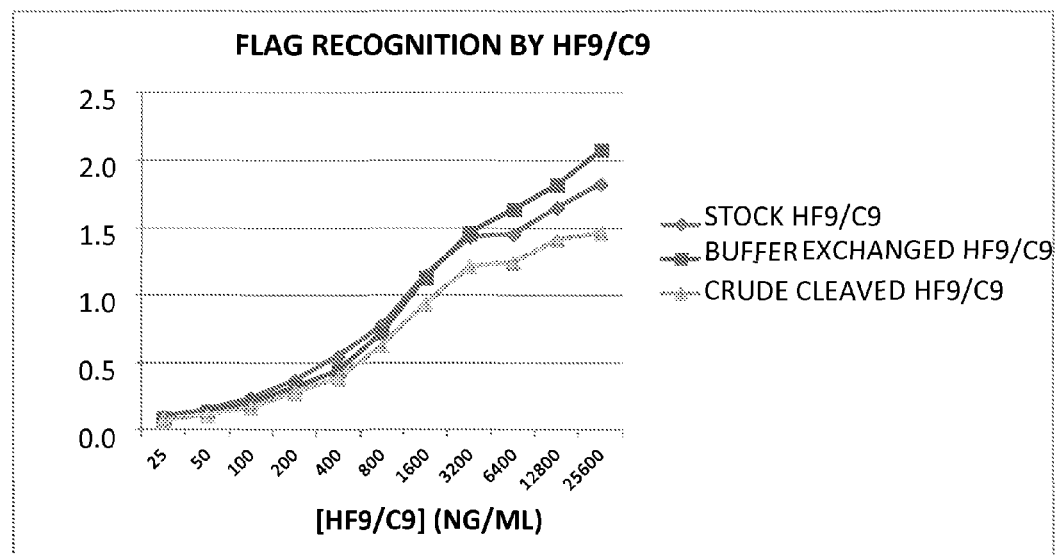

Key to FIG. 4:
25 AAEM
26 Incubation
27 Immobilised Biomolecule
28 Wash
29 Cleavage
30 Unmodified 'Native' Biomolecule FIG. 5 is a graph showing FLAG epitope recognition by HF9/C9 antibody that has been bound to and released from a 1,3-dikeotester resin.

Figure 6:
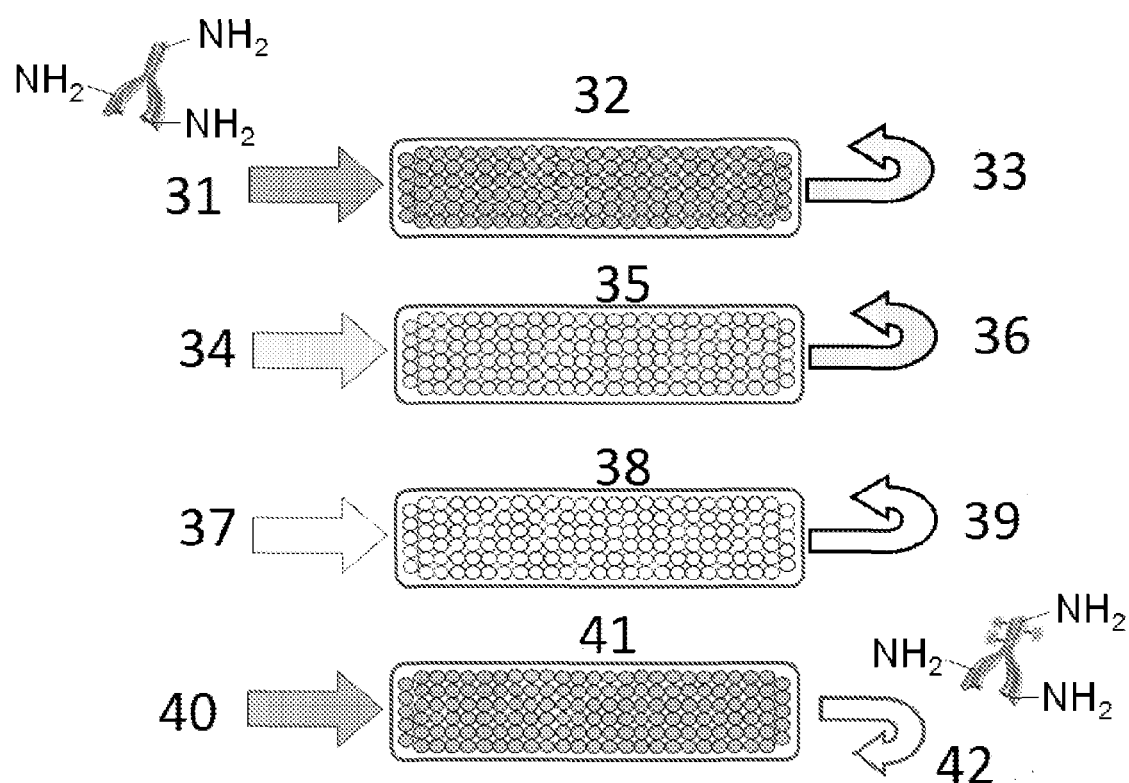

FIG. 6 is a cartoon representation of the lock-release process carried out in Example 12.

Figure 7:
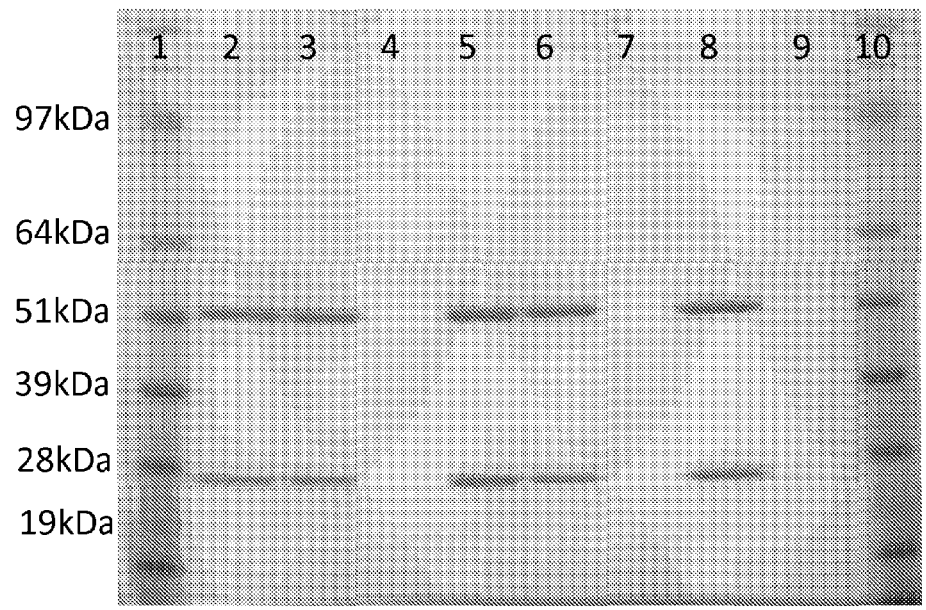

Key to FIG. 6:
31 HF9/C9 Antibody
32 STEP 1: Immobilise MAb on beads
33 Waste disposal
34 On-resin modification of MAb (2-IT or partial reduction)
35 STEP 2: Modification of MAb whilst bound to beads to give free-SH groups
36 Waste disposal
37 TAG (F-Maleimide)
38 STEP 3: TAG, Label or small peptide binds to immobilised MAb (Conjugate formation)
39 Waste disposal
40 Release Agent
41 STEP 4: Cleaves Conjugate from beads
42 Purified HF9/C9 CONJUGATE FIG. 7 is a photo of a reducing gel loaded with fluorescein HF9/C9 conjugates.

Figure 8:

FIG. 8 is a photo of a non-reducing gel loaded with fluorescein HF9/C9 conjugates.

Figure 9:
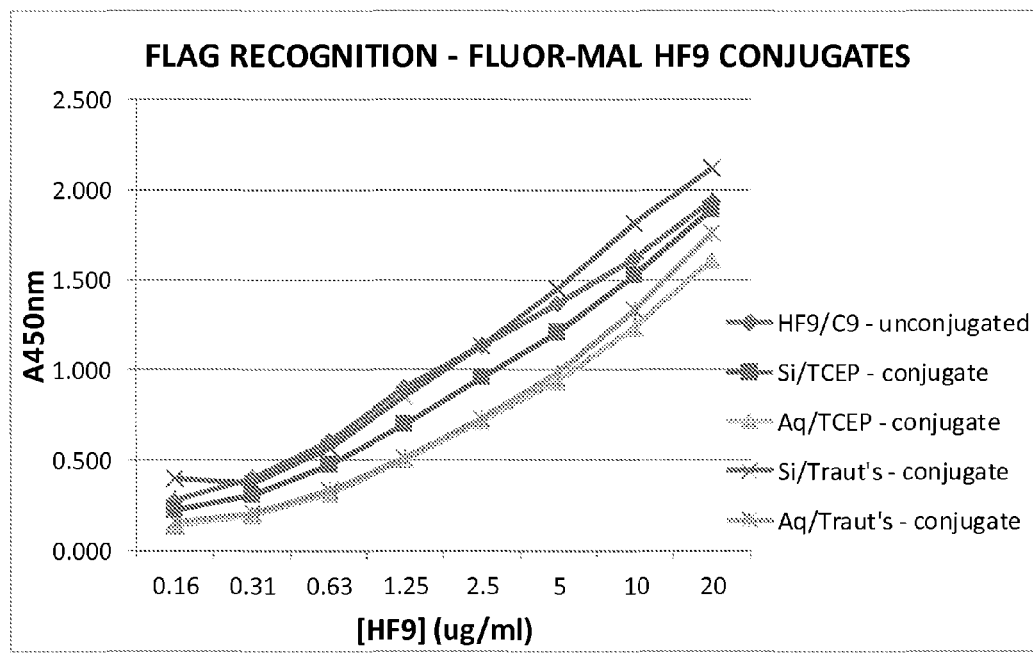

FIG. 9 is a graph showing FLAG epitope recognition by fluorescein HF9/C9 conjugated antibody that has been bound to and released from a 1,3-diketoester resin. Antibody conjugates modified using TCEP and Traut's reagent are compared.

Figure 10:
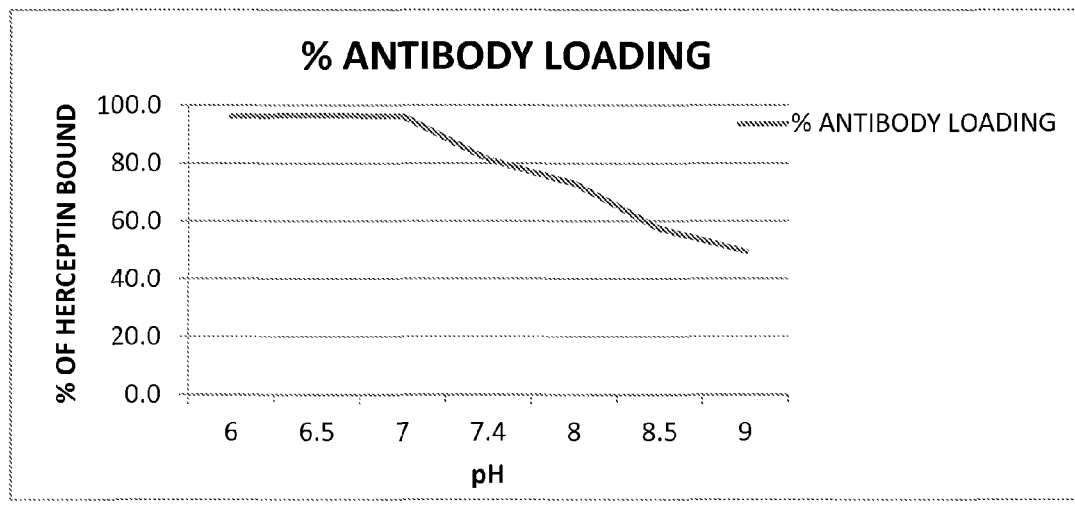

FIG. 10 is a graph showing the % Herceptin bound to the support versus pH.

Figure 11:
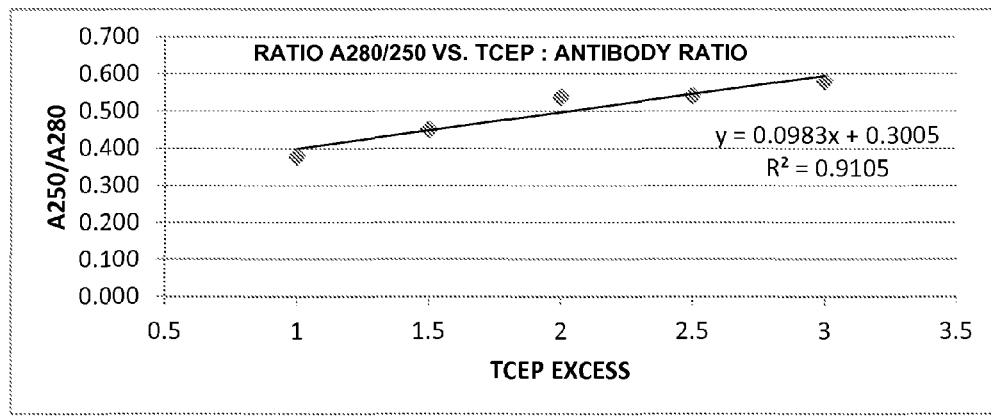

FIG. 11 is a graph showing the Absorbance at A250/A280 versus the amount of TCEP reducing agent.

Figure 12:
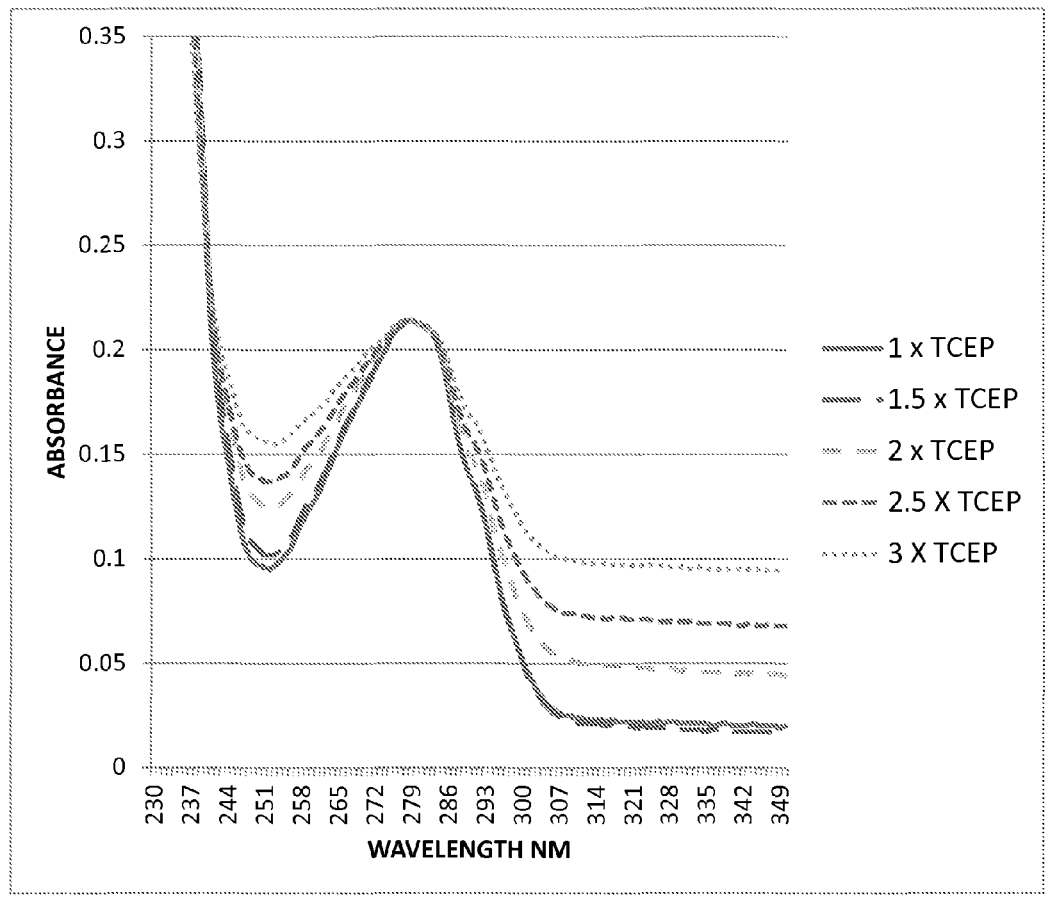

FIG. 12 is a graph showing a graph showing the absorbance spectrum of an antibody drug conjugate versus the amount of TCEP reducing agent.

Additives such as buffer salts, detergents, disaccharide stabilisers, preservatives, etc.). As the biomolecule is locked to a solid bead it is simply retained during a filtration step.

In locking a biomolecule to a solid support, such as a bead, movement of the attached biomolecule is physically restricted. In a process stream containing a high load of biomolecule the locking of the biomolecule to a solid support affords a high concentration of the desired substance. Applying this approach to a flow system in which the solid phase beads are contained within a column further enhances the physical containment of the desired biomolecule. Biomolecules, such as antibodies, are often very high value substances and therefore physical containment in a concentrated manner is seen as a level of insurance to accidental loss, discharge and contamination. Solid phase immobilization of the biomolecule minimizes the human error factor during processing.

Furthermore, the storage of a biomolecules such as an antibody in a concentrated manner infers a consistency to the tertiary and quaternary structure form of the biomolecule. Whilst the biomolecule is locked to the bead it is not subjected to large swings in concentration which when applied to a concentrated solution of a biomolecule could lead to precipitation and or aggregation issues.

Likewise, when a biomolecule such as an antibody is locked to a solid support it is more stable to changes in buffer composition including co-solvent concentration. In a concentrated solution of a biomolecule such changes may lead to undesirable precipitation and or aggregation effects.

Locking a biomolecule to a solid phase support is an advantageous storage format. The immobilized biomolecule may be stored in a concentrated manner but not have to undergo additional manipulations such as multiple freeze-thaw cycles which are known to be detrimental to biomolecules such as proteins and antibodies. A solid physical format for storage makes for a more controllable means for dispensing samples. As the biomolecule is not solvated the potential for adventitious bioburden and or endotoxin contamination is less of a concern.

Using a 'lock-release' process of the present invention, the manufacturing plant size to produce 1 kg of antibody can be reduced to only 10 liters, meaning that systems of the present invention can be retrofitted into existing facilities. This results in reducing production cost and eliminates capital expenditure.

The lock between the biomolecule and the support of the invention is a covalent bond. The releasable binding, without affecting the structure and integrity of the biomolecule, represent a significant advantage for the derivatised supports of the invention. This bond may be considered to be 'semi-permanent', and is a result of a functional group that is comprised on the support. The functional group is selected from 1,3-ketoester, 1,3-ketothioester and 1,3-ketoamide. The support is said to be derivatised with these functional groups. The derivatised support has an affinity for primary amine groups. Primary amine groups can be found on a wide range of biomolecules.

In addition to the standard aqueous buffers referred to herein, suitable solvents include DMA (N,N-dimethylacetamide), NMP (N-Methylpyrrolidone), DMSO, MeCN, propylene glycol and polyethylene glycol. Preferably, the buffer is an aqueous buffer. By mixing a solution of a biomolecule with the derivatised support an enamine bond is formed. No additional reagents or extreme processing conditions are required. The biomolecule is selectively attached to the derivatised support and all other materials that do not comprise a primary amine group do not bind to the support. Therefore, excess reagents, contaminants, by-products and impurities from the process liquor can be washed away (e.g. detergents can be removed). Because the biomolecule is immobilised on the derivatised support it is retained during each washing step. This proposed purification method is simple and may be enhanced by performing the 'lock-release' method in a column under flow conditions. Advantageously, the locking is reversible. Treatment with a release reagent and/or adjusting the pH can release the biomolecule. The 'lock-release' method can be applied to commercial manufacture of antibodies and antibody based therapeutics such as Antibody Drug Conjugates (ADCs), as well as small-scale production for R&D use.

The locking chemistry on the derivatised support is highly selective and may only be released by exposure to the correct release reagent or by adjusting the pH. As a result, the immobilised biomolecule may be treated with a variety of different chemicals or undergo further reactions whilst still attached to the support without breaking the bond between the support and the biomolecule. This could be advantageous for synthesising antibody based therapeutics such as Antibody Drug Conjugates (ADCs). This approach is attractive when dealing with potent antibody based drugs where a high level of containment is required. The approach allows the assembly of ADCs in a concentrated and less hazardous manner than that currently employed in the industry.

An important quality of an ADC is the average number of drugs that are conjugated (the Drug Antibody Ratio, also known as DAR) because this determines the amount of payload of drug that can be delivered to a target site and can affect both safety and efficacy of the ADC. Using methods of the present invention, an ADC having a particular desired DAR may be produced. For example, an ADC may be produced having a DAR of between 1-10, such as between 1-5, e.g. a DAR of 2, 3, or 4.

A variety of methods have been used to measure the DAR, depending on the properties of the drug and how it is linked to the antibody (i.e., the site of conjugation and structure of the linker). One technique relies on a UV/VIS spectroscopic analysis of the ADC. This method requires that the UV/VIS spectra of the drug and/or linker and of the antibody have different $A_{max}$ values. Using the measured absorbances of the ADC and the extinction coefficients of the antibody at its $A_{max}$ of ~280 nm and the drug and/or linker at its $A_{max}$, the individual concentrations of antibody and drug and/or linker can be determined. From this, the molar ratio (moles of drug per mole of antibody) can be calculated. For example, the drug linker may absorb at 254 nm. In contrast protein absorbs characteristically at 280 nm and contributes minimally at 254 nm. Therefore, UV absorption at 254 nm can be attributed to the drug-linker. Therefore, in an antibody conjugate containing a drug-linker there is a direct linear relationship between A280 & A254 scans.

In all cases, contribution of the drug or drug-linker to the measured absorbance at 280 nm must be incorporated into the calculation of the protein concentration, as must any contribution of the protein to the absorbance at the drug and/or drug linker $A_{max}$.

Orthogonal methods to verify the validity of the spectroscopic technique can be used, including use of radiometric methods (conjugation with radiolabeled drugs) and chromatographic methods such as hydrophobic interaction chromatography (HIC) separation for quantification of individual drug loaded species. SEC and HIC analysis are the preferred methods for determining the DAR of an ADC. Both chromatography techniques compliment UV & Gel electrophoresis.

The derivatised support only reacts with primary amines. The support will not react with other functional groups such as thiols, secondary amines, carboxylic acids, alcohols and guanidines. Primary amines are immobilised onto the derivatised support through the formation of an enamine chemical bond. The enamine bond is stabilised through hydrogen bonding which is proposed to be the basis of functional selectivity of the derivatised support. Therefore in a mixture of various functional groups, the derivatised support will only react with primary amines. In terms of proteins and other biomolecules the derivatised support will react with Lysine, Nα-amino, Ornithine, etc. It is Lysine residues and N-amino groups of an antibody or a peptide that are targeted to lock on to the derivatised support.

The enamine bond can be treated with cleavage agents, such as pH altering agents and/or release reagents to unlock of the biomolecule and release it in an unmodified form. This is an important feature of the 'lock-release' process. Upon treatment with a cleavage agent the biomolecule is returned in a form that maintains biological activity. That is to say it is returned in its 'native state'.

The cleavage conditions may take one of several forms such:
  A pH Switch—increasing pH>8, pH>10 is optimal.
  Nucleophilic addition by small nucleophile, e.g. a high concentration of hydrazine
  Exposure to high concentration of Lysine or other primary amine source.

This approach allows release of a high level of immobilised biomolecules from the derivatised support.

Scaling up the process, e.g. by binding a greater amount of biomolecule to the resin, results in reducing the percentage loss of biomolecule from the process. In other words, one advantage of the present invention is that, upon scaling up the reaction, a higher proportion of the theoretical binding can be achieved thereby making the process amenable to large scale use. This may be due to a lower percentage of biomolecule being lost during the process of the invention.

There are a number of factors that play an important role when handling and storing biomolecules in accordance with the present invention.

These include:
  Media—an aqueous buffer (e.g. PBS) environment is preferred. However, biomolecules such as antibodies can withstand some solvent mixtures. It is preferred that the ratio should not exceed 10% of solvent in aqueous buffer. Suitable solvents are DMSO, MeCN, DMF, propylene glycol, polyethylene glycol.
  pH—biomolecules are preferentially handled in neutral pH (~7). However, some biomolecules such as antibodies can be manipulated in media between pH 5 to 10 for several hours without detrimental effects.
  Concentration—Typical working concentration of an antibody process stream is 1-10 mg/ml.
  Activity—Testing for activity before and after manipulations can be achieved using ELISA assays.
  Yield—Quantification of the amount of biomolecule removed from the bead can be determined using specialised methods.

The process may be performed in a batch or flow manner. Flow techniques are advantageous and commercially attractive as the beads can be tightly packed into a column reducing the area required to perform manipulation. In addition, by flowing a solution of biomolecule through the column the binding efficiency increases significantly. This process can be performed in a shorter time than the same reaction performed in batch mode (that is a suspension of the bead in a solution of the biomolecule). Overall, the throughput of the manipulation is enhanced in flow mode. This minimises waste as the process is performed in a concentrated, contained manner.

The 'lock-release' system provided by the present invention provides the following advantages:
  Significant overall cost reduction
  Robust and reproducible technique with minimal yield loss
  Scalable to meet the demands of manufacturing aspirations
  Minimal capex outlay (avoids expensive equipment)
  A technique that allows a 'hold point' or long term storage of the immobilised biomolecule
  Minimises waste and environmental impact
  Easy to operate without specialist knowledge ('plug-and-play')

There is a significant advantage in covalently attaching biomolecules such as antibodies to beads. The intrinsic value of a batch of purified antibody for use in a clinical trial is extremely high. For example, using standard techniques production of 150 gram (0.150 kg) of antibody for a customer to use in a Phase I clinical trial, the materials cost can be up to $5 million. Using standard techniques the conjugation reaction to make an Antibody Drug Conjugate (ADC) is performed in solution at high dilution. There is a risk of loss of the valuable antibody through operator error or unforeseen failure of a piece of equipment. The 'lock-release' concept of the present invention reduces these risks. Locking the antibody to a bead has an 'insurance policy' associated with the technique. The biomolecule is locked onto the bead in a concentrated and discreet manner. It is now physically difficult to lose the biomolecule from the process.

Most standard methods of storing biomolecules emphasize that biomolecules should be kept at reduced temperatures. Traditionally, biomolecules can be stored between +1 to +5° C. for short periods or frozen at temperatures below −20° C. for prolonged periods. The 'lock-release' system of the present invention can be used to immobilise the biomolecule to a solid support and store in a dry form. After storage the biomolecule can be released from the bead. It is possible to store the biomolecule attached to the bead in a dry form for prolonged periods, such as up to 1 week, 1 month, 6 months or 12 months. The 'lock-release' concept may be used for the long term storage of antibodies.

Suitable beads include 'off-the-shelf' PS-DVB beads. These beads are uniform spherical in nature and are amenable to batch and flow technologies. PS-DVB beads are based on a DVB-polystyrene matrix. When the % content of DVB in the bead composition is ~2% it infers that the bead is highly swellable in organic solvents. As the bead is porous the internal matrix is fully accessible to reagents in this media. This type of bead composition can be termed 'Microporous'. However, in water based systems microporous beads do not swell. Consequently, the large majority of the functional sites that might bind to a biomolecule are not accessible and binding is reduced.

In an embodiment the bead is a macroporous bead. Many manipulations carried out on biomolecules are performed in water based systems. For PS-DVB the issue of water incompatibility in the context of the present invention is overcome by manipulating the bead composition. The % DVB content of the beads of the present invention is around 5-60%, for example 10-50%, 10-40%, 10-30%, or 20-25%. This results in the bead being more rigid and significantly less prone to swelling. Indeed, a bead of this composition does not swell at all in aqueous systems. This type of bead composition can be termed 'Macroporous'.

A 'macroporous' support contains a higher percentage composition of DVB compared to a microporus support. Although a 'macroporous' support has an identical internal porous matrix/network to a 'microporous' support its higher DVB composition fixes this matrix as a rigid network. Thus a 'macroporous' matrix does not undergo swelling. By removing the issue of adequate solvation/swelling a macroporous support may be used in any media environment; aqueous, semi-aqueous or organic. The internal matrix remains accessible regardless of the environmental media.

Similarly, a silica support can be used in aqueous, semi-aqueous or organic media as they are free from swelling. Thus, the derivatised support of the present invention also encompasses Silica beads. Silicas are highly suited to aqueous environments, readily available at tonne scale and relatively cheap.

The following beads can be derivatised with 1,3-ketoester groups and/or 1,3-ketothioester groups and/or 1,3-ketoamide groups:
  PL-DVB (OH, microporous PS-1% DVB)
  Davisil LC1000 Å (OH, irregular shaped silica, Supplier: Grace)
  MS-Gel D-50-1000 Å (OH, spherical, porous, high purity silica)
  QuadraPure BZA (NH2, macroporous PS-20% DVB, Supplier: Johnson Matthey)
  Hydroxymethyl PS(OH, microporous PS-1% DVB, Supplier: Novabiochem)
  Aminomethyl PS(NH2, microporous PS-1% DVB, Supplier: Novabiochem)
  NovaSyn TentaGel (NH2, grafted PEG-PS, Supplier: Novabiochem).

The following support may also be derivatised in accordance with the present invention: QuadraPure™ (spherical, porous microporous & macroporous beads based DVB-PS) and QuadraSil™ (a porous, spherical silica) both sold by Johnson Matthey.

The derivatised support preferably comprises solid beads that are preferentially spherical in nature and of uniform size. Using a porous bead has the added advantage of increasing the surface area and therefore capacity (that is the amount of biomolecule that can be attached per gram of bead).

An important characteristic for purification of biomolecules is the pore size of any porous bead. Selectively may be inferred by the restriction of access of the biomolecule to the highly functional internal matrix. The beads of the present invention comprise pores that are of an amenable size for immobilising biomolecules as shown below.

| | Pore Size | | | |
|---|---|---|---|---|
| | 100 Å | 300 Å | 1000 Å | 2000-4000 Å |
| Used for immobilising | Small organic molecules, small peptides, small nucleotides. | Polypeptides & globular proteins. | Fibrous proteins | Very large bio macromolecules |

The pore sizes of the derivatised support of the present invention is selected from about 100 Å, about 300 Å, about 1000 Å and about 2000-4000 Å. A pore size of 1000 Å is appropriate for the purification of antibodies.

Scheme 1 shows the mechanism by which a biomolecule comprising a primary amine group is immobilised onto a support functionalised with a diketone. An enamine bond formed between the functionalised support and the biomolecule to form a support-biomolecule compound. The enamine bond is stabilised by hydrogen bonding and making the diketone group selective for primary amine groups only. The support-biomolecule compound is washed to remove compounds that do not contain a primary amine group.

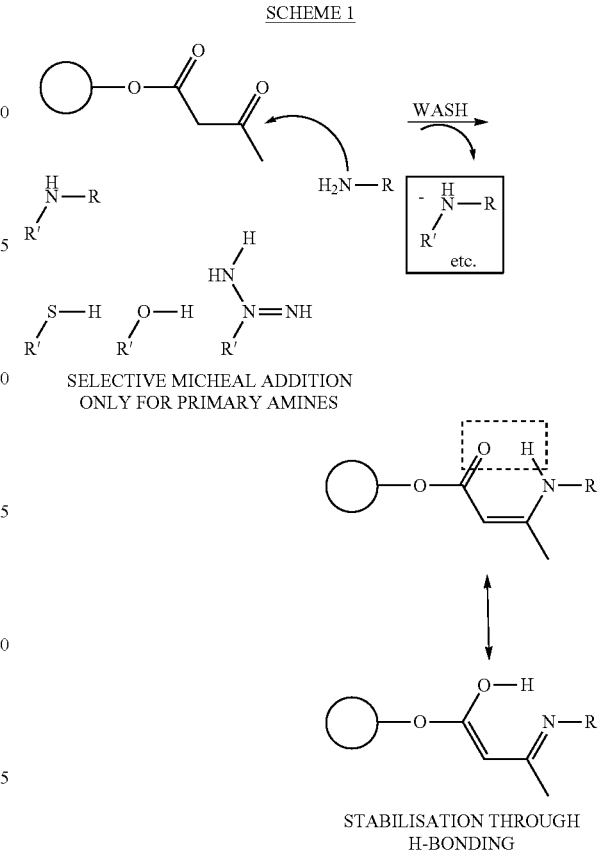

SCHEME 1

SELECTIVE MICHEAL ADDITION
ONLY FOR PRIMARY AMINES

STABILISATION THROUGH
H-BONDING

EXAMPLES

Example 1. Synthesis of Diketone Derivatised Support

The following approach can be used for delivering diketone functional groups to a support. Using primary hydroxyl or primary amino based supports as a starting point the diketone functionality can be introduced by the formation of the corresponding 1,3-diketoester, 1,3-diketothioester or 1,3-diketoamide respectively.

The following 2 reagents were used for derivatisation. These are:

(i) Dioxinone
(ii) tert-Butyl acetoacetone

Diketone functional supports can be furnished through mobilizing the support in toluene containing approximately 5 equiv. of either reagent above at elevated temperatures. Conversion requires <3 hrs and in the case of derivatising an amino support the reaction can be followed by the Kaiser support test.

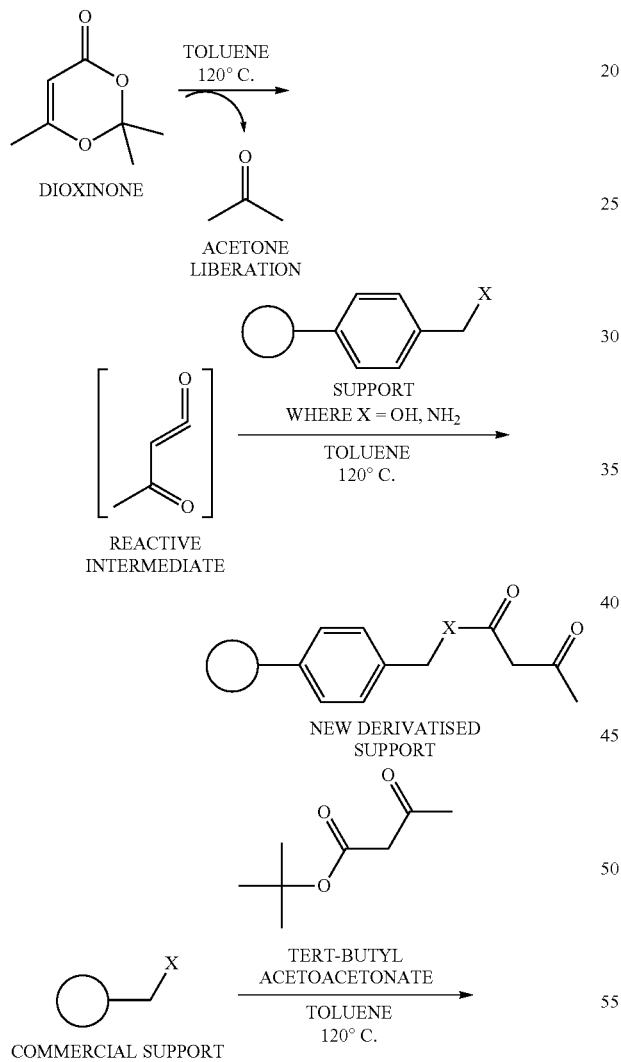

Example 2.1. Immobilisation of an Amino Acid to a Diketone Derivatised Support

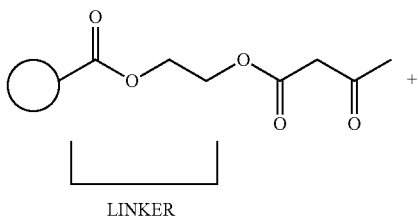

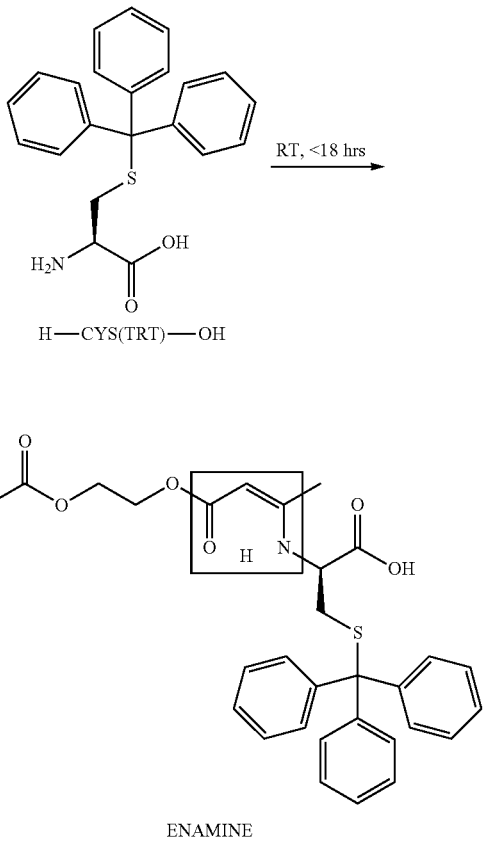

An amino acid was immobilised to a diketone derivatised support to form a support-amino acid compound. H-Cys(Trt)-OH is a small, well characterised and defined zwitterionic amino acid that contains a UV chromophore. 50 mg/ml solutions of H-Cys(Trt)-OH in (i) DMF, or (ii) DMSO were incubated with 5 molar equiv of diketone derivatised support at ambient temperature with gentle agitation over an 18 hr period. Verification of the immobilisation of was confirmed by RP-HPLC analysis. The absence of H-Cys(Trt)-OH in the elution profile indicated complete immobilisation of the amino acid. The resultant support-amino acid compound was then washed sequentially with 10 aliquots of fresh solvent and filtered. The resin was then further washed with 5 aliquots of dichloromethane then the resin was collapsed with methanol and dried 'in-vacuo' to constant weight.

Example 3. Cleavage of Biomolecule from Support-Biomolecule Compound Using Hydrazine as a Release Reagent A biomolecule was cleaved from a biomolecule-support compound using hydrazine as a release reagent. The cleavage reaction was carried out in 5% v/v solution in DMF at room temperature for one hour. The postulated cleavage mechanism is shown below.

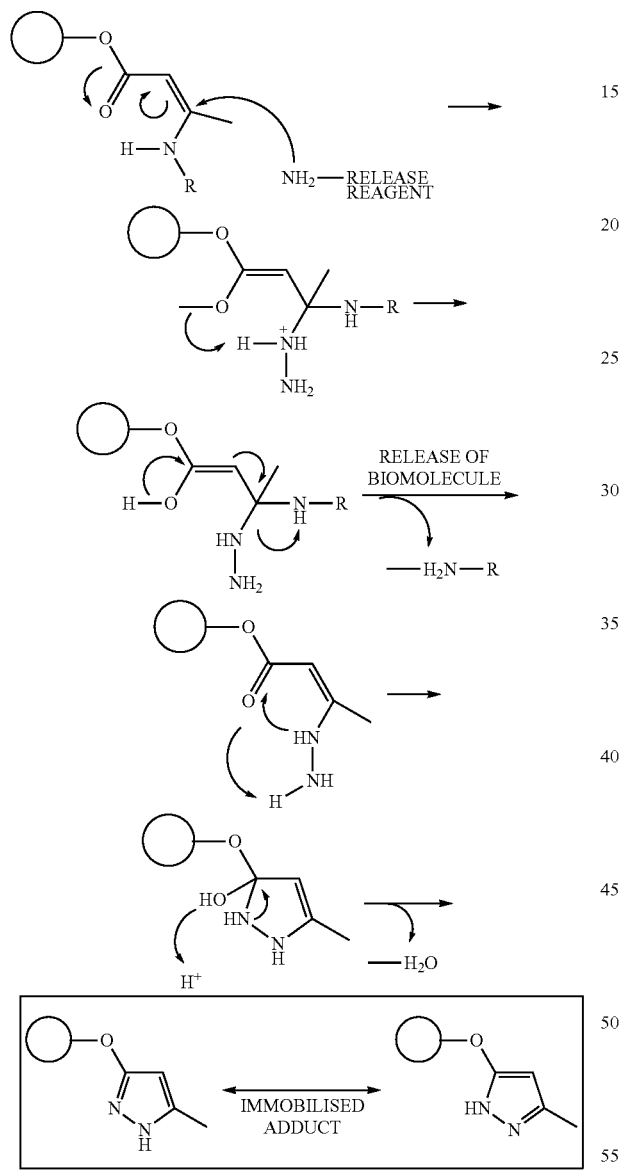

Example 4. Cleavage of Biomolecule from Support-Biomolecule Compound Using Various Release Reagents A several gram batch of H-Cys(Trt)-OH immobilised on diketone derivatised support was prepared. 20 mg Samples of immobilised H-Cys(Trt)-OH were then incubated in the following 5% v/v hydrazine solutions: 5% v/v hydrazine in DMF; 5% v/v hydrazine in DMSO; 5% v/v hydrazine in MeOH; 5% v/v hydrazine in MeCN. The cleavage reaction was monitored by RP-HPLC using a standard of H-Cys(Trt)-OH (1 mg/ml). The reaction was carried out at 40° C. for one hour.

It was shown that hydrazine can release the amino acid in <1 hr. Importantly, the material released is unmodified. A co-injection of the crude media from the reaction & a standard of H-Cys(Trt)-OH verified this.

In a similar manner other reagents were investigated using this proven model. It was found that 1M $NH_3$ in MeOH, 5% $NH_2OH$ and Ethanolamine are also suitable cleavage agents. All released the H-Cys(Trt)-OH in an unmodified manner in <1 hr. These studies indicate that enamine bond formation is reversible.

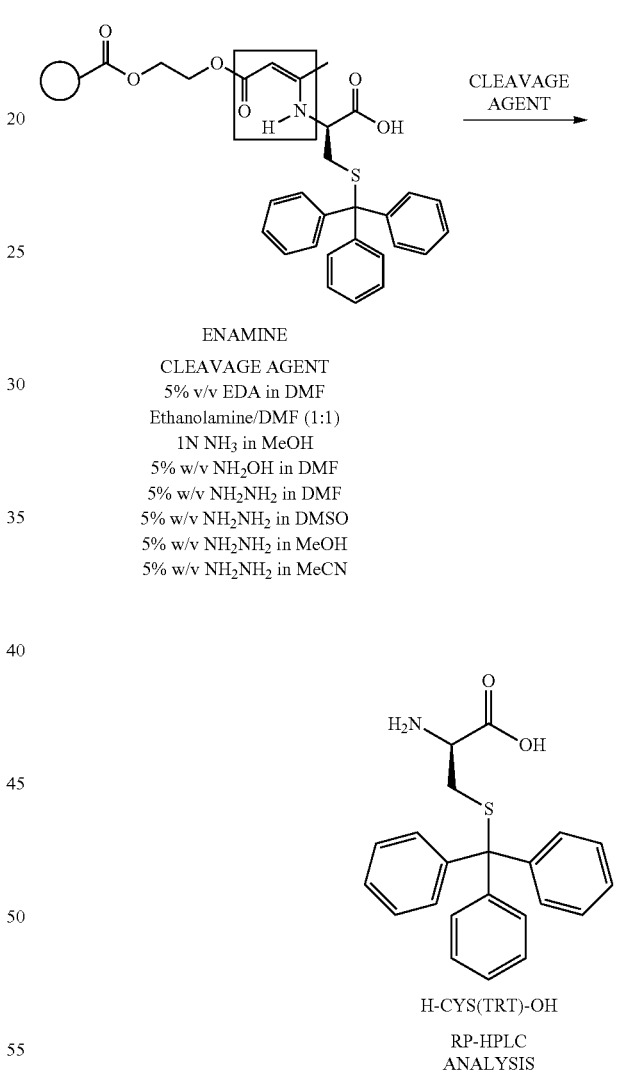

Example 5. Cleavage of a Peptide from Support-Biomolecule Compound Using Various Release Reagents A peptide was immobilised to diketone derivatised support to form a support-peptide compound. Verification of the immobilisation of was confirmed by RP-HPLC. The support was then washed with fresh DMF and filtered. A 5 mg sample of the support-peptide compound was then suspended in a 2 ml solution of 5% v/v NH$_2$NH$_2$ in DMF for 1 hr at 40° C. A representative sample of the suspension was analysed by RP-HPLC against a 1 mg/ml standard of H-[Leu]$^5$-enkephalin-OH. The elution profile indicated the presence of the peptide in an unmodified state.

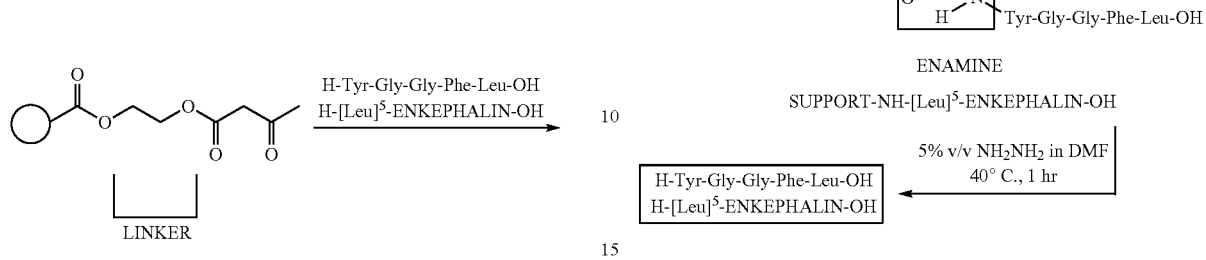

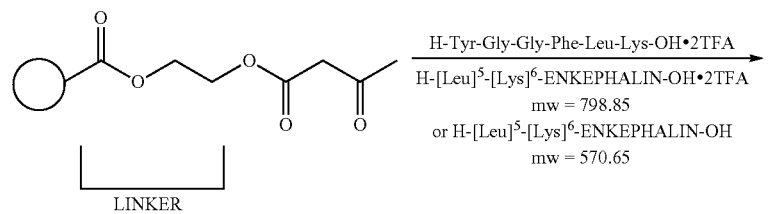

Example 6.5. Second Peptide Example (Enamine Formation Via Nε-Amino Group from Lysine or Nα-Amino Group)

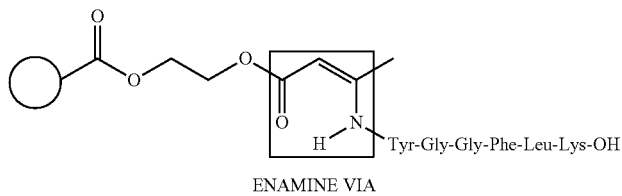

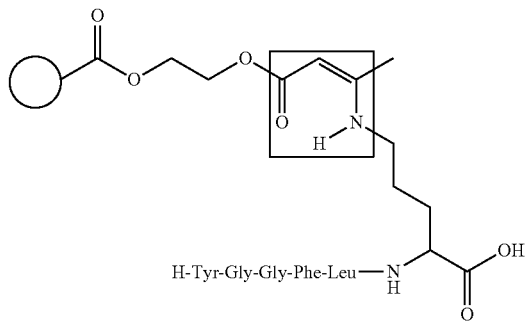

H-[Leu]$^5$-[Lys-Nε-SUPPORT)]$^6$-ENKEPHALIN-OH

Media
5mg H-[Leu]$^5$-[Lys]$^6$-ENKEPHALIN-OH in 2ml DMF
5mg H-[Leu]$^5$-[Lys]$^6$-ENKEPHALIN-OH in 2ml 10% Py in DMF

Example 7. Immobilisation of an Antibody to a Diketone Derivatised Support 3 different support supports were derivatised with functional groups 1,3-ketoester and 1,3-ketoamide. The supports were incubated with a 150 KD antibody, namely HF9/C9, in 3 different environments. HF9/C9 is an antibody that has been raised against an 11 residue peptide (CHDDYKKK-KKK) and recognises the FLAG epitope.

2 ml of antibody HF9/C9 at a concentration of 1 mg/ml was applied separately to three derivatised supports. The first support was derivatised QuadraPure™ BZA (Johnson Matthey). The second support was QuadraPure™ AK (Johnson Matthey). The third support was derivatised Silica. 300 mg of support was used for each incubation. Antibodies were incubated with each support in PBS, 10% DMSO or 80% DMSO. The incubation was carried out at 37° C. at pH 7.4 for 1 hour, 3 hours or 18 hours. The binding results are depicted in table 1 and table 2.

TABLE 1

Concentration (μg/ml) of mAb remaining after binding for 1, 3, or 18 h

| | 1 h Binding | | | 3 h Binding | | | 18 h Binding | | |
|---|---|---|---|---|---|---|---|---|---|
| | PBS | 10% | 80% | PBS | 10% | 80% | PBS | 10% | 80% |
| QPBZA | 917 | 743 | — | 570 | 626 | — | 83 | 263 | — |
| QPAK | 902 | 828 | — | 921 | 756 | — | 935 | 1049 | — |
| Si | 3.6 | 839 | — | 4.3 | 840 | — | 0.5 | 1120 | — |

TABLE 2

Total mAb bound (mg)

| | 1 h Binding | | | 3 h Binding | | | 18 h Binding | | |
|---|---|---|---|---|---|---|---|---|---|
| | PBS | 10% | 80% | PBS | 10% | 80% | PBS | 10% | 80% |
| QPBZA | 0.166 | 0.514 | — | 0.860 | 0.748 | — | 1.834 | 1.474 | — |
| QPAK | 0.196 | 0.344 | — | 0.158 | 0.488 | — | 0.13 | 0 | — |
| Si | 1.993 | 0.322 | — | 1.991 | 0.320 | — | 1.999 | 0 | — |

The results show that the antibody bound most effectively in PSB buffer. The most effective support for antibody binding was silica. Almost 100% binding was observed after 1 hour.

Example 8. Release of an Antibody from a Diketone Derivatised Support

Cleavage was initiated with 2 ml 5% v/v hydrazine in PBS buffer/DMSO (9:1) at pH7.4, 37° C. for 3 hours. The results are shown in table 3.

TABLE 3

Concentration (ug/ml) of mAb cleaved from support by hydrazine.

| | PBS | | | 10% DMSO | | |
|---|---|---|---|---|---|---|
| | μg/ml cleaved | Total (mg) | Recovery (%) | μg/ml cleaved | Total (mg) | Recovery (%) |
| QPBZA | 40.4 | 0.022 | 1.1 | 50.6 | 0.024 | 1.2 |
| QPAK | 0 | 0 | 0 | 0.8 | 0 | 0 |
| Si | 1052 | 0.526 | 26.3 | 327 | 0.157 | 7.9 |

The released antibody was intact and biologically active.

Example 9. Immobilisation of an Antibody to a 1,3-Diketoester Derivatised Silica The reaction was scaled up to use 20 mg of antibody. A 10 ml solution of the 150 KD antibody HF9/C9 at concentration 2 mg/ml in PBS was applied to 1.5 g of 1,3-diketoester derivatised Silica (1000 Å) for binding. The incubation was carried out at room temperature at pH 7.4. Samples taken at 30 min, 60 min, 120 min & 180 min for analysis to determine quantity of antibody bound. Analysis was performed using quantitative Bradford assay and quantitative ELISA assay.

Quantitative ELISA:—Immobilisation of HF9/C9

| Time Point | [Protein] (μg/ml) | Protein unbound (mg) | % Locked to 1,3-diketoester Silica |
|---|---|---|---|
| 30 min | 83 | 0.83 | 96 |
| 60 min | 74 | 0.74 | 96 |
| 120 min | 102 | 1.02 | 95 |
| 180 min | 85 | 0.85 | 96 |
| Post-Filtration | 86 | 0.86 | 96 |

After 30 mins both the Bradford & ELISA assays revealed that 80 μg/ml (800 μg total) HF9/C9 remained unbound. 96% of antibody was bound to the derivatised Silica. Scaling up the reaction resulted in increasing the percentage of antibody locked to the silica.

After 180 mins the Silica containing bound antibody was transferred to a sinter and filtered under gentle vacuum. The Silica containing bound antibody was further washed with 2×10 ml PBS collected upon a sinter by vacuum filtration.

Example 10. Release of an Antibody from a 1,3-Diketoester Derivatised Silica Cleavage of HF9/C9 from the Silica was initiated with 5% v/v hydrazine in PBS for 90 mins at room temperature. The Silica was then collected upon a glass sinter and the filtrate collected. The silica was washed sequentially with 2×10 ml aliquots of PBS, pH 7.4 and the filtrates collected and combined. The resultant filtrate was then buffer-exchanged into PBS by centrifugation (3,500×g at +4 C) via Vivaspin™ 20 membrane cartridges (50 kDa molecular weight cut off).

Quantitative Bradford assay & A280 UV spectrometry confirmed a 78% recovery of HF9/C9 from the Si resin. Similarly, quantitative ELISA determined a recovery of 70% following buffer exchange. Loses of up to 1 mg of the antibody to the Vivaspin™ membranes were anticipated in this procedure. When the reaction is scaled up, the percentage loss of biomolecule decreases.

Quantitative ELISA:—Release of HF9/C9

|  | [Protein] (µg/ml) | Total Protein (mg) | % Recovery |
|---|---|---|---|
| Crude cleaved HF9/C9 | 1,254 | 12.54 | 63 |
| Buffer-exchanged (desalted) HF9/C9 | 1,389 | 13.9 | 70 |

The crude cleaved HF9/C9 antibody & buffer-exchanged HF9/C9 antibody are comparable to stock material for recognition of the specific peptide target FLAG epitope. Activity of the antibody is fully maintained throughout the immobilisation and release procedures. The results from the ELISA sandwich assay FLAG recognition study are shown in FIG. 5.

Analysis by Reducing & Non-Reducing NuPAGE demonstrates that cleaved HF9/C9 antibody remains structurally intact & shows identical banding patterns to the stock HF9/C9 control. Structural integrity has been maintained throughout the 'Lock-Release' process steps.

Example 11. Saturation Capacity of 1,3-Diketoester Derivatised Silica (1000 Å)

5 ml of the HF9/C9 150 KD Antibody at concentration 2 mg/ml in PBS was applied to derivatised silica for binding. The following weights of derivatised silica were used for the study
(i) 0.5 g, (ii) 0.25 g and (iii) 0.125 g All incubations were performed at room temperature at pH 7.4. A time course study was undertaken over 18 hrs. The saturation capacity of 1,3-diketoester derivatised Silica (1000 Å) was determined by Bradford Assay & UV A280.

Bradford Assay Results:

| Time | Drivatised Silica (mg) | [HF9/C9] unbound (mg/ml) | HF9 bound (mg) | Experimental Silica saturation capacity (µg/mg resin) |
|---|---|---|---|---|
| 30 min | 125 | 0.84 | 5.8 | 46.4 |
|  | 250 | 0.38 | 8.1 | 32.4 |
|  | 500 | 0.08 | 9.6 | — |
| 1 h | 125 | 0.85 | 5.7 | 45.6 |
|  | 250 | 0.43 | 7.9 | 31.6 |
|  | 500 | 0.07 | 9.7 | — |
| 2 h | 125 | 0.85 | 5.7 | 45.6 |
|  | 250 | 0.41 | 7.9 | 31.6 |
|  | 500 | 0.08 | 9.6 | — |
| 3 h | 125 | 0.87 | 5.6 | 45.1 |
|  | 250 | 0.41 | 7.9 | 31.6 |
|  | 500 | 0.08 | 9.6 | — |
| 4 h | 125 | 0.87 | 5.7 | 45.6 |
|  | 250 | 0.42 | 7.9 | 31.6 |
|  | 500 | 0.08 | 9.6 | — |
| 18 h | 125 | 0.85 | 5.8 | 46.4 |
|  | 250 | 0.45 | 7.8 | 31.2 |
|  | 500 | 0.06 | 9.7 | — |

All samples achieved saturation capacity within the first sampling time point of 30 mins. No further improvement in antibody binding was noted over time. No leakage of the antibody was noted over the 18 hr time period indicating binding was permanent. Analysis by Bradford assay indicated the capacity of the derivatised Silica (1000 Å) for the 125 & 250 mg sample runs to be 31-46 µg/mg (31-46 mg/g). All 10 mg of HF9/C9 antibody was bound by 500 mg of silica.

Example 12. Conjugation of HF9/C9 150 KD Antibody with Fluoroscein-5-Maleimide In a set of experiments the fluorescent labelling agent fluorescein-5-maleimide was conjugated to the HF9/C9 150 KD antibody. The immunofluorescent label provides a fast, visual indication that a conjugation reaction has occurred. Fluoroscein-5-maleimide is introduced to the antibody through a thiol functional group. The reactive maleimide group on the immunofluorescent label reacts with thiol groups on the antibody to form a permanent thioether covalent bond. The maleimide chemistry used in this experimental set mirrors many commercial conjugation processes for ADCs. Fluoroscein-5-maleimide therefore provides a mimic of a maleimide reactive cytotoxic drug-linker.

The aim of the experimental set was to synthesise the conjugate Fluorescein-HF9/C9 using the 'Lock-Release' technique and compare with analogous conjugations performed in solution phase. The 'Lock-Release' experiments required that the conjugation reaction be performed whilst the antibody was immobilised on 1,3-diketoester derivatised Silica (1000 Å) and consequently released from the solid phase support by a chemical key.

Four Model Fluorescein-HF9/C9 conjugates synthesised in parallel.
(A) HF9/C9 conjugation with fluorescein-5-maleimide using partial tris 2-carboxyethyl phosphine (TCEP) reduction
  (i) synthesised via 'Lock-Release' Solid Phase
  (ii) synthesised via Solution Phase
(B) HF9/C9 conjugation with fluorescein-5-maleimide using 2-iminothiolane (2-IT, Trauts Reagent) derivatisation of Lysine
  (iii) synthesised via 'Lock-Release' Solid Phase
  (iv) synthesised via Solution Phase The solution phase experiments did not include the support of the invention and were carried out to compare the lock-release method of the invention to a stand solution phase procedure.

The key process steps for the 'Lock-Release' technique is represented in FIG. 6.

A Fluorescein-Antibody Ratio (also referred to as Drug Antibody Ratio, DAR) was targeted in each experimental set. This experiment shows that it is possible to vary the amount of drug bound to the antibody. For partial reduction using TCEP a DAR of 4 was targeted. For Traut's reagent a DAR between 2.0-2.5 was targeted (A)(i) HF9/C9 Conjugation with Fluorescein-5-Maleimide Using Partial TCEP Reduction—Synthesised via 'Lock-Release' Solid Phase Immobilisation of HF9/C9 to 1,3-diketoester derivatised silica—10 ml of the 150 KD HF9/C9 antibody at a concentration of 2 mg/ml was applied to 1.5 g of 1,3-diketoester derivatised Silica (1000 Å) in PBS for binding. The incubation was performed at pH 7.4 at room temperature over 18 hr duration. Antibody HF9/C9 binding was monitored spectrophotometrically by A280. Samples were removed at 30 mins, 1 hr & 18 hrs. A280 analysis determined 92% of the HF9/C9 antibody was immobilised upon the derivatised silica after 30 mins. No further improvement in antibody binding was noted over time. No leakage of the antibody was noted over the 18 hr time period indicating binding was permanent. After 18 hours the silica was transferred to a sinter and washed with 2 sequential 10 ml aliquots of PBS, pH 7.4.

Partial Reduction of HF9/C9 Antibody—Partial reduction of HF9/C9 antibody was performed following 'Bioconjugate Techniques' protocol (page 96/97, Greg T. Hermanson, Academic Press; 2nd edition, 2008, ISBN-13: 978-0123705013). The Silica with the immobilised antibody was suspended in 5 ml of PBS at pH 7.4 containing 5 mM EDTA. To partially reduce the disulphides in the hinge region while maintaining a biospecific antibody this protocol recommends using a 2.75 fold molar excess of TCEP over that of the antibody concentration. For 20 mg of HF9/C9 this required 0.1 mg of TCEP. A single 50 µl aliquot of TCEP stock solution at a concentration of 2 mg/ml in PBS at a pH of 7.4 was added to the silica slurry giving a total TCEP mass of 0.1 mg. The reaction was then incubated at room temperature for 2 hours.

Removal of TCEP reagent—The derivatised silica was transferred to a sinter and washed with 2 sequential 10 ml aliquots of PBS, pH 7.4 to remove excess TCEP.

Conjugation of Fluorescein-5-Maleimide to modified HF9/C9—Silica with immobilised & modified antibody was re-suspended in 5 ml of PBS containing 5 mM EDTA at pH 7.4. The Fluorescein-5-Maleimide was then added in a molar excess over the molar amount of sulfhydryl to be coupled. Assuming there are 4 free sulphydryl groups present per antibody and 20 mg of HF9/C9 antibody has been immobilised to the silica a 22 fold excess of fluorescein-5-maleimide was employed. A single 100 µl aliquot of fluorescein-5-maleimide at a concentration of 51 mg/ml in DMSO was added to the slurry. Upon addition of the fluorescein-5-maleimide the reaction turned bright orange. The resulting slurry was incubated for 2 hours at room temperature. The reaction was sampled after 1 hour and the absorbance at 495 nm was recorded. Analysis shows that as the immunofluorescent label is in such an excess it is not possible to monitor the progression of the conjugation reaction by A495.

Removal of Fluorescein-5-Maleimide reagent by washing—After the 2 hour conjugation reaction had been reached the silica was filtered on to a glass sinter and washed with 10 sequential 10 ml aliquots of PBS, pH 7.4 to remove excess unconjugated Fluorescein-5-Maleimide. The filtrate from the final wash was analysed by A495 and was shown to contain no free unconjugated fluorescein-5-maleimide. The silica was visibly pale orange in appearance.

In this step excess fluorescein-5-maleimide reagent was not quenched but washed away showing the utility of a heterogeneous process thereby omitting a 'quenching step'.

Cleavage of the fluorescein-Antibody Conjugate from Silica—The washed silica was re-suspended in 10 ml of 5% v/v hydrazine in PBS, pH 7.4 (10 ml). The suspension was incubated at room temperature for a 90 min duration to cleave the antibody conjugate from the silica. Cleavage was monitored by A280.

Washing the silica to remove all traces of Conjugate— The resultant hydrazine slurry was filtered through a porosity 3 glass sinter. A 25 ml RB flask was used to collect the neat hydrazine-antibody conjugate filtrate. A gentle vacuum was used to remove residual filtrate from the silica. The desired filtrate containing fluorescein-HF9/C9 conjugate was immediately transferred to a collection vessel. Assuring a minute residence time for each wash charge the spent silica was washed with 4 sequential 5 ml aliquots of PBS, pH 7.4. The filtrates were combined and collected for analysis.

Washes were collected in two lots of 10 ml volumes and tested for protein at A280. Wash one was found to contain protein however wash two contained only trace amounts. After the cleavage step the silica was no longer orange and had returned to white in colour. The filtrate however was deep orange.

The filtrate was tested at A280 and A495 and the conjugation was shown to be successful with approximately 2.9 moles of immunofluorescent label per mole of HF9/C9 antibody.

The combined filtrates were then desalted with fresh PBS, pH 7.4 using Vivaspin™ columns (MW 5000 cut-off).

(A)(ii) HF9/C9 Conjugation with Fluoroscein-5-Maleimide Using Partial TCEP Reduction—Synthesised via Solution Phase Partial Reduction of HF9/C9 Antibody—Partial reduction of HF9/C9 antibody was performed following 'Bioconjugate Techniques' protocol (page 96/97, Greg T. Hermanson, Academic Press; 2nd edition, 2008, ISBN-13: 978-0123705013). To partially reduce the disulphides in the hinge region while maintaining a biospecific antibody this protocol recommends using a 2.75 fold molar excess of TCEP over that of the antibody concentration. For 20 mg of HF9/C9 this required 0.1 mg of TCEP. A single 50 µl aliquot of TCEP solution at a concentration of 2 mg/ml in PBS at a pH of 7.4 was added to 10 ml of HF9/C9 150 KD antibody at a concentration of 2 mg/ml in PBS containing 5 mM EDTA at pH 7.4. The reaction was then incubated at room temperature for 2 hours.

Removal of TCEP reagent—The TCEP reagent was removed from the solution using Vivaspin™ columns with a MW 50000 cut-off. This required multiple spins and took approx. 1 hour in total.

Conjugation of Fluorescein-5-Maleimide to modified HF9/C9—From the Vivaspin™ columns the antibody was buffer exchanged into 5 ml of PBS at pH 7.4 containing 5 mM EDTA. The Fluorescein-5-Maleimide was then added in a 22 molar excess over the molar amount of sulfhydryl to be coupled. A single 100 µl aliquot of fluorescein-5-maleimide at a concentration of 51 mg/ml in DMSO was added to the antibody solution. Upon addition of the fluorescein-5-maleimide the reaction solution turned bright orange. The resulting solution was incubated for 2 hours at room temperature. The reaction was sampled after 1 hour and the absorbance at 495 nm was recorded. Analysis shows that as the immunofluorescent label is in such an excess it is not possible to monitor the progression of the conjugation reaction by A495.

Removal of Fluorescein-5-Maleimide reagent by washing—The excess unconjugated immunofluorescent label was removed using Vivaspin™ columns with MW 50000 cut-off. This required multiple spins as the excess immunofluorescent label was very difficult to remove using the membrane Vivaspin™ technique. In total to remove excess fluorescein-5-maleimide from the solution phase conjugation required 4 hrs of spinning on Vivaspin™ columns. The resultant conjugated was in a desalted form.

The desalted conjugate was tested at A280 and A495 and the conjugation reaction was shown to be successful with approximately 4.0 moles of immunofluorescent label per mole of HF9/C9 antibody.

(B)(iii) HF9/C9 Conjugation with Fluoroscein-5-Maleimide Using 2-IT (Trauts Reagent) Derivatisation of Lysine— Synthesised Via 'Lock-Release' Solid Phase Immobilisation of HF9/C9 to 1,3-diketoester derivatised silica—10 ml of the 150 KD HF9/C9 antibody at a concentration of 2 mg/ml was applied to 1.5 g of 1,3-diketoester derivatised Silica (1000 Å) in PBS for binding. The incubation was performed at pH 7.4 at room temperature over an 18 hr duration. Antibody HF9/C9 binding was monitored spectrophotometrically by A280. Samples were removed at 30 mins, 1 hr & 18 hrs. A280 analysis determined 92% of the HF9/C9 antibody was immobilised upon the derivatised silica after 30 mins (92%). No further improvement in antibody binding was noted over time. No leakage of the antibody was noted over the 18 hr time period indicating binding was permanent. After 18 hours the silica was transferred to a sinter and washed with 2 sequential 10 ml aliquots of PBS, pH 7.4.

Lysine modification with Traut's reagent (2-IT)—Immobilised antibody on silica was re-suspended in 5 ml of PBS containing 5 mM EDTA at pH 8.0. The EDTA reagent is required to chelate metal ions in solution preventing sulfhydryl oxidation. Depending of the size of the proteins and the degree of thiolation required a 2 to 20 fold excess of Traut's to protein concentration is recommended (Thermo Scientific. *Instructions Traut's Reagent*. Available: http://www.piercenet.com/instructions/2160414.pdf). A 2 mg/ml (14 mM) stock solution of Traut's reagent in PBS at pH 8 was prepared immediately before use. A single 90 µl aliquot was charged directly to the slurry containing the immobilised antibody. This equates to a Traut's reagent mass of 0.18 g at 10 molar equivalents with respect to antibody concentration. The resultant slurry was then incubated for 1 hour at room temperature.

Removal of Traut's reagent—After 1 hr reaction time the derivatised silica was transferred to a sinter and washed with 2 sequential 10 ml aliquots of PBS, pH 7.4 to remove excess Traut's reagent.

Conjugation of Fluorescein-5-Maleimide to modified HF9/C9—Silica with immobilised & modified antibody was re-suspended in 5 ml of PBS containing 5 mM EDTA at pH 7.4. The Fluorescein-5-Maleimide was then added in a molar excess over the molar amount of sulfhydryl to be coupled. Assuming there are 4 free sulphydryl groups present per antibody and 20 mg of HF9/C9 antibody has been immobilised to the silica a 22 fold excess of fluorescein-5-maleimide was employed. A single 100 µl aliquot of fluorescein-5-maleimide at a concentration of 51 mg/ml in DMSO was added to the slurry. Upon addition of the fluorescein-5-maleimide the reaction turned bright orange. The resulting slurry was incubated for 2 hours at room temperature. The reaction was sampled after 1 hour and the absorbance at 495 nm was recorded. Analysis shows that as the immunofluorescent label is in such an excess it is not possible to monitor the progression of the conjugation reaction by A495.

Removal of Fluoroscein-5-Maleimide reagent by washing—After the 2 hour conjugation reaction had been reached the silica was filtered on to a glass sinter and washed with 10 sequential 10 ml aliquots of PBS, pH 7.4 to remove excess unconjugated Fluorescein-5-Maleimide. The filtrate from the final wash was analysed by A495 and was shown to contain no free unconjugated fluorescein-5-maleimide. The silica was visibly pale orange in appearance.

In this step excess fluorescein-5-maleimide reagent was not quenched but washed away showing the utility of a heterogeneous process thereby omitting a 'quenching step'. No quenching was required to kill the reactive group since it was possible to wash excess fluorescein-5-maleimide reagent away.

Cleavage of the Fluorescein-Antibody Conjugate from Silica—The washed silica was re-suspended in 10 ml of 5% v/v hydrazine in PBS, pH 7.4 (10 ml). The suspension was incubated at room temperature for a 90 min duration to cleave the antibody conjugate from the silica. Cleavage was monitored by A280.

Washing the silica to remove all traces of Conjugate—The resultant hydrazine slurry was filtered through a porosity 3 glass sinter. A 25 ml RB flask was used to collect the neat hydrazine-antibody conjugate filtrate. A gentle vacuum was used to remove residual filtrate from the silica. The desired filtrate containing fluorescein-HF9/C9 conjugate was immediately transferred to a collection vessel. Assuring a minute residence time for each wash charge the spent silica was washed with 4 sequential 5 ml aliquots of PBS, pH 7.4. The filtrates were combined and collected for analysis. Washes were collected in two lots of 10 ml volumes and tested for protein at A280. Wash one was found to contain protein however wash two contained only trace amounts. After the cleavage step the silica was no longer orange and had returned to white in colour. The filtrate however was orange. The filtrate was tested at A280 and A495 and the conjugation was shown to be successful with approximately 1.1 moles of immunofluorescent label per mole of HF9/C9 antibody.

The combined filtrates were then desalted with fresh PBS, pH 7.4 using Vivaspin™ columns (MW 5000 cut-off).

(B)(iv) HF9/C9 Conjugation with Fluoroscein-5-Maleimide Using 2-IT (Trauts Reagent) Derivatisation of Lysine—Synthesised Via Solution Phase Lysine modification with Traut's reagent (2-IT)—A 2 mg/ml (14 mM) stock solution of Traut's reagent in PBS at pH 8 was prepared immediately before use. A single 90 µl aliquot of Traut's reagent was charged directly to a 10 ml solution of HF9/C9 150 KD antibody at a concentration of 2 mg/ml in PBS containing 5 mM EDTA at pH 7.4. This equates to a Traut's reagent mass of 0.18 g at 10 molar equivalents with respect to antibody concentration. The resultant solution was then incubated for 1 hour at room temperature.

Removal of Traut's reagent—After 1 hr reaction time the Traut's reagent was removed from the solution using Vivaspin™ columns with a MW 50000 cut-off. This required multiple spins and took approx. 1 hour in total.

Conjugation of Fluorescein-5-Maleimide to modified HF9/C9—From the Vivaspin™ columns the antibody was buffer exchanged into 5 ml of PBS at pH 7.4 containing 5 mM EDTA. The Fluorescein-5-Maleimide was then added in a 22 molar excess over the molar amount of sulfhydryl to be coupled. A single 100 µl aliquot of fluorescein-5-maleimide at a concentration of 51 mg/ml in DMSO was added to the antibody solution. Upon addition of the fluorescein-5-maleimide the reaction solution turned bright orange. The resulting solution was incubated for 2 hours at room temperature. The reaction was sampled after 1 hour and the absorbance at 495 nm was recorded. Analysis shows that as the immunofluorescent label is in such an excess it is not possible to monitor the progression of the conjugation reaction by A495.

Removal of Fluoroscein-5-Maleimide reagent by washing—The excess unconjugated immunofluorescent label was removed using Vivaspin™ columns with MW 50000 cut-off. This required multiple spins as the excess immunofluorescent label was very difficult to remove using the membrane Vivaspin™ technique. In total to remove excess fluorescein-5-maleimide from the solution phase conjugation required 4 hrs of spinning on Vivaspin™ columns. The resultant conjugated was in a desalted form.

The desalted conjugate was tested at A280 and A495 and the conjugation reaction was shown to be successful with approximately 2.2 moles of immunofluorescent label per mole of HF9/C9 antibody.

Analysis & Monitoring of Reactions
Binding Results

Binding of HF9/C9 to silica was monitored by A280 & Bradford assay at various time-points. The time course is represented below.

A280

| Time | Reducing agent used | Experimental A280 result | [HF9/C9] unbound (mg/ml) | HF9/C9 immobilised (mg) |
|---|---|---|---|---|
| 30 min | TCEP | 0.149 | 0.11 | 18.9 |
| | Traut's | 0.176 | 0.13 | 18.7 |
| 1 hour | TCEP | 0.180 | 0.13 | 18.7 |
| | Traut's | 0.222 | 0.16 | 18.4 |
| 18 hour | TCEP | 0.238 | 0.18 | 18.2 |
| | Traut's | 0.265 | 0.2 | 18 |

Bradford Assay Results

The concentration of HF9/C9 remaining unbound at all sampling time points was lower than the sensitivity of the assay. This indicated that all available HF9/C9 antibody had been immobilised to the derivatised silica. This information was used for calculation of the quantities of TCEP/Traut's as well as Fluorescein-maleimide to be used for conjugation (i.e. assume 20 mg HF9/C9 was coupled).

Conjugation Results

Both TCEP & Traut's reagent proved to be effective reducing agents enabling the conjugation of fluorescein-5-maleimde to the HF9/C9 antibody in both solution and solid phase environments. The extent of labelling is shown in the table below.

A280/A495

| Reducing agent used | Silica/ Aqueous | Experimental A280 result | Experimental A495 result | [HF9/C9] (mg/ml) | Yield Fluorescein-HF9/C9 (mg) | Labelling ratio |
|---|---|---|---|---|---|---|
| TCEP | Si | 0.268 | 0.197 | 2 | 14 | 2.9 |
| | Aq | 0.692 | 0.646 | 5.1 | 25 | 4 |
| Traut's | Si | 0.248 | 0.078 | 1.84 | 11.9 | 1.1 |
| | Aq | 0.652 | 0.379 | 4.8 | 21 | 2.2 |

Yield of Fluoroscein-HF9/C9 antibody conjugate from the 'Lock-Release' solid phase process employing TCEP was ≥77%, determined by A280. Similarly, the yield from the 'Lock-Release' process employing Traut's reagent was ≥66%. Anticipated yield loss resulted from the Vivaspin™ membrane desalt steps and operator manipulations transferring silica to sinter or reaction vessel in several steps.

Structural Integrity of Conjugate

To determine structural integrity of all fluorescein HF9/C9 conjugates reducing and non-reducing NuPAGE analysis were performed. A 2 μg aliquot of each sample loaded per lane. Running buffer=1×MOPS.

The reducing gel is depicted in FIG. 7 and the lanes were loaded with the following:
1. Marker
2. Si/TCEP
3. Aq/TCEP
4. PBS
5. Si/Traut's
6. Aq/Traut's
7. PBS
8. HF9/C9—non-conjugate
9. PBS
10. Marker In all cases two bands of ~50 & 25 kDA representing the characteristic Heavy & Light chains respectively were apparent. No evidence of contaminants or degradation was evident. All treatments correlate with the banding pattern of unmodified HF9/C9 antibody.

The Non-Reducing Gel is Depicted in FIG. 8 and the Lanes were Loaded with the Following:
1. Marker
2. Si/TCEP
3. Aq/TCEP
4. PBS
5. Si/Traut's
6. Aq/Traut's
7. PBS
8. HF9/C9—non-conjugate
9. PBS
10. Marker In each of the 2 examples the fluorescein HF9/C9 conjugates synthesised using the 'Lock-Release' solid phase technique does not appear significantly different from the analogous conjugate synthesised using traditional solution phase techniques. As anticipated, TCEP treatment has resulted in reduction of disulphide bonds & shows evidence of Heavy & Light chains as well as whole antibody. Treatment with Traut's reagent shows similar patterns to the HF9/C9 control material.

Antibody Activity

The results from the ELISA sandwich assay FLAG recognition study clearly demonstrate that Fluorescein-HF9/C9 conjugates made by 'Lock-Release' & solution phase techniques have identical antibody activity as naked antibody for FLAG recognition. The results are shown in FIG. 9.

Example 13. Immobilisation of Herceptin Antibody to a 1,3-Diketoester Derivatised Silica A 1.0 ml stock sample of Herceptin 150 KD antibody at a concentration of 25 mg/ml in formulation buffer was double desalted using a disposable PD-10 column containing Sephadex™ G-25 packing material (GE Healthcare, 1.45×5.0 cm (8.3 ml) packed bed dimensions). The Herceptin antibody was buffer exchanged into PBS, pH 7.4 to afford a Herceptin stock solution with protein concentration of 20.5 mg/ml.

A series of Herceptin concentrations in PBS buffer, pH 7.4 were prepared using the aliquots and dilutions noted in the table below:

| [Her] desalted stock solution (mg/ml) | Desired [Her] (mg/ml) | Fold Dilution | Vol. PBS for dilution (ml) | Volume of [Her] stock solution required | Total Volume at desired [Her] (ml) |
|---|---|---|---|---|---|
| 20.5 | 1 | 20 | 3.8 | 0.2 | 4.0 |
| 20.5 | 2 | 10 | 0.9 | 0.1 | 1.0 |

-continued

| [Her] desalted stock solution (mg/ml) | Desired [Her] (mg/ml) | Fold Dilution | Vol. PBS for dilution (ml) | Volume of [Her] stock solution required | Total Volume at desired [Her] (ml) |
|---|---|---|---|---|---|
| 20.5 | 4 | 5 | 0.8 | 0.2 | 1.0 |
| 20.5 | 6 | 3.33 | 0.7 | 0.3 | 1.0 |
| 20.5 | 8 | 2.5 | 0.6 | 0.4 | 1.0 |

Individual 1.0 ml aliquots of 150 KD antibody Herceptin solution at concentrations 1.0 mg/ml, 2.0 mg/ml, 4.0 mg/ml, 6 mg/ml & 8 mg/ml in PBS were applied to 0.1 g of 1,3-diketoester derivatised Silica (1000 Å) for binding. The incubation was carried out at room temperature at pH 7.4. Samples taken at 180 mins for analysis to determine quantity of antibody bound. After 180 mins the silica was washed with 4 aliquots of fresh PBS, pH 7.4. Analysis was performed using quantitative A280 spectrophotometry. A standard plot of Herceptin at 1 mg/ml affords an Absorbance of 1.5 Abs units. Experimental Abs readings were compared to the calibration plot to determine Herceptin concentration [Her] in mg/ml. Each of the wash fractions was analysed to accurately determine the quantity of antibody unbound using A280 (sum of Abs values from washes).

Quantitative A280:—Immobilisation of Herceptin

| Time Point | [Her] concentration (mg/ml) | Herceptin unbound (Abs) | Mass Herceptin unbound | Mass Herceptin bound (mg per 100 mg Silica) |
|---|---|---|---|---|
| 180 min | 1 | 0.282 | 0.19 | 0.81 |
| 180 min | 2 | 0.999 | 0.67 | 1.33 |
| 180 min | 4 | 3.443 | 2.30 | 1.70 |
| 180 min | 6 | 6.077 | 4.05 | 1.95 |
| 180 min | 8 | 8.637 | 5.76 | 2.24 |

The results concluded that the higher the concentration of Herceptin in PBS, pH 7.4 the higher the experimental binding capacity of the silica. Within this set of experiments the loading capacity was >22.4 mg/ml at pH 7.4.

Example 14. Immobilisation of an Antibody to a 1,3-Diketoester Derivatised Silica—Effect of Buffering pH A 1.0 ml stock sample of Herceptin 150 KD antibody at a concentration of 25 mg/ml in formulation buffer was double desalted using a disposable PD-10 column containing Sephadex™ G-25 packing material (GE Healthcare, 1.45×5.0 cm (8.3 ml) packed bed dimensions). The Herceptin antibody was buffer exchanged into 30.5 ml of PBS, pH7.4 to afford a protein concentration of 0.82 mg/ml.

A 1.22 ml solution of the 150 KD antibody Herceptin in PBS was applied to 0.1 g of 1,3-diketoester derivatised Silica (1000 Å) for binding. The incubation was carried out at room temperature at a range of pH values. The study utilises PBS at the following pH values:
(i) 6
(ii) 6.5
(iii) 7
(iv) 7.4
(v) 8
(vi) 8.5
(vii) 9

PBS, pH 7.4 was pH was adjusted with base using 0.2 mM NaOH(aq.) and with acid using 0.1 M Acetic acid(aq.). Samples were taken at 60 min & 300 min for analysis to determine quantity of unbound antibody. Analysis was performed using quantitative A280 spectrophotometric analysis.

A280:—Immobilisation of Herceptin

| Time Point | pH | Conc. (mg/ml) | Volume charged (ml) | Herceptin unbound (Abs) | Herceptin unbound (mg) | Herceptin bound (mg) | % Locked to 1,3-diketoester Silica |
|---|---|---|---|---|---|---|---|
| 60 min | 6 | 0.78 | 1.22 | 0.052 | 0.035 | 0.895 | 96.3 |
| 300 min | 6 | 0.78 | 1.22 | 0.043 | 0.029 | 0.901 | 96.9 |
| 60 min | 6.5 | 0.78 | 1.22 | 0.047 | 0.031 | 0.899 | 96.6 |
| 300 min | 6.5 | 0.78 | 1.22 | 0.044 | 0.029 | 0.901 | 96.8 |
| 60 min | 7 | 0.78 | 1.22 | 0.052 | 0.035 | 0.895 | 96.3 |
| 300 min | 7 | 0.78 | 1.22 | 0.062 | 0.041 | 0.889 | 95.6 |
| 60 min | 7.4 | 0.82 | 1.22 | — | — | — | — |
| 300 min | 7.4 | 0.82 | 1.22 | 0.282 | 0.188 | 0.812 | 81.2 |
| 60 min | 8 | 0.82 | 1.22 | 0.403 | 0.269 | 0.731 | 73.1 |
| 300 min | 8 | 0.82 | 1.22 | 0.365 | 0.243 | 0.757 | 75.7 |
| 60 min | 8.5 | 0.82 | 1.22 | 0.640 | 0.427 | 0.573 | 57.3 |
| 300 min | 8.5 | 0.82 | 1.22 | 0.569 | 0.379 | 0.621 | 62.1 |
| 60 min | 9 | 0.82 | 1.22 | 0.757 | 0.505 | 0.495 | 49.5 |
| 300 min | 9 | 0.82 | 1.22 | 0.704 | 0.469 | 0.531 | 53.1 |

See FIG. 10.

The results indicate that the optimum loading of Herceptin onto 1,3-diketoester derivatised silica (1000 Å) is between pH 6 to 7. A minimum of 96% of the antibody was bound to the silica support after 60 mins incubation at room temperature. Extending the incubation time from 1 hr to 5 hrs had neither a positive nor negative effective on the antibody loading capacity.

Example 15. Comparative Immobilisation of Two Antibodies to a 1,3-Diketoester Derivatised Silica—Effect of pH A 2.5 ml stock sample of Herceptin 150 KD antibody at a concentration of 25 mg/ml in formulation buffer was double desalted using a disposable PD-10 column containing Sephadex™ G-25 packing material (GE Healthcare, 1.45×5.0 cm (8.3 ml) packed bed dimensions). The Herceptin antibody was buffer exchanged into PBS, pH 7.4 to afford a Herceptin stock solution with protein concentration of 8.56 mg/ml. A 1 mg/ml Herceptin solution in PBS pH 7.4 was prepared using this double desalted stock solution by dilution with PBS, pH 7.4.

A stock solution of purified 150 KD antibody HF9/C9 at a concentration of 2 mg/ml was diluted with PBS pH 7.4 to furnish HF9/C9 antibody solution at the desired concentration of 1 mg/ml.

Separately, three 2.0 ml aliquots of each antibody:
(i) double desalted 150 KD antibody Herceptin in PBS pH 7.4, or
(ii) 150 KD antibody HF9/C9 in PBS pH 7.4
were pH adjusted to the following pH values:
a) 6.5
b) 7.4 (for Herceptin) & 7.2 (for HF9/C9)
c) 8.5 pH was adjusted from pH 7.4 with base using 0.2 mM NaOH(aq.) or with acid using 0.1 M Acetic acid(aq.).

To each antibody sample was charged 0.1 g of 1,3-diketoester derivatised Silica (1000 Å) for binding. The incubation study was performed at room temperature at the range of pH values noted above.

Samples were taken at 60, 180 & 300 mins for analysis to determine quantity of unbound antibody. Analysis was performed using quantitative A280 spectrophotometric analysis. A standard plot of Herceptin at 1 mg/ml affords an Absorbance of 1.5 Abs units. Similarly, a standard plot of HF9/C9 at 1 mg/ml affords an Absorbance of 1.24 Abs units.

The results of the binding study are noted in the tables below:

Quantitative A280:—Comparative Immobilisation of Herceptin & HF9/C9 Antibody

| Time Point | Antibody | pH | [Antibody] concentration (mg/ml) | Volume charged to Silica (ml) | Antibody unbound (Abs at 280 nm) | Mass of Antibody unbound Mg) | Mass Antibody bound (mg per 100 mg Silica) | % Antibody bound |
|---|---|---|---|---|---|---|---|---|
| 60 min | Herceptin | 6.5 | 1 | 2 | 0.190 | 0.127 | 1.873 | 93.67 |
| 60 min | HF9/C9 | 6.5 | 1 | 2 | 0.096 | 0.077 | 1.923 | 96.13 |
| 60 min | Herceptin | 7.4 | 1 | 2 | 0.518 | 0.345 | 1.655 | 82.73 |
| 60 min | HF9/C9 | 7.2 | 1 | 2 | 0.187 | 0.187 | 1.849 | 92.46 |
| 60 min | Herceptin | 8.5 | 1 | 2 | 0.942 | 0.628 | 1.372 | 68.60 |
| 60 min | HF9/C9 | 8.5 | 1 | 2 | 0.919 | 0.741 | 1.259 | 62.94 |
| 180 min | Herceptin | 6.5 | 1 | 2 | 0.184 | 0.123 | 1.877 | 93.87 |
| 180 min | HF9/C9 | 6.5 | 1 | 2 | 0.137 | 0.110 | 1.890 | 94.48 |
| 180 min | Herceptin | 7.4 | 1 | 2 | 0.468 | 0.312 | 1.688 | 84.40 |
| 180 min | HF9/C9 | 7.2 | 1 | 2 | 0.168 | 0.135 | 1.865 | 93.23 |
| 180 min | Herceptin | 8.5 | 1 | 2 | 0.869 | 0.579 | 1.421 | 71.90 |
| 180 min | HF9/C9 | 8.5 | 1 | 2 | 0.900 | 0.726 | 1.274 | 63.71 |

| Time Point | Antibody | pH | [Antibody] concentration (mg/ml) | Volume charged to Silica (ml) | Antibody unbound (Abs at 280 nm) | Mass of Antibody unbound Mg) | Mass Antibody bound (mg per 100 mg Silica) | % Antibody bound |
|---|---|---|---|---|---|---|---|---|
| 300 min | Herceptin | 6.5 | 1 | 2 | 0.206 | 0.137 | 1.863 | 93.13 |
| 300 min | HF9/C9 | 6.5 | 1 | 2 | 0.124 | 0.100 | 1.900 | 95.00 |
| 300 min | Herceptin | 7.4 | 1 | 2 | 0.424 | 0.283 | 1.717 | 85.87 |
| 300 min | HF9/C9 | 7.2 | 1 | 2 | 0.184 | 0.148 | 1.852 | 92.58 |
| 300 min | Herceptin | 8.5 | 1 | 2 | 0.843 | 0.562 | 1.438 | 71.90 |
| 300 min | HF9/C9 | 8.5 | 1 | 2 | 0.902 | 0.727 | 1.273 | 63.63 |

The results indicate a trend for the Herceptin & HF9/C9 antibodies. The optimal pH to maximise binding of either antibody to the derivatised 1,3-diketoester derivatised Silica (1000 Å) in this study is pH 6.5. For Herceptin & HF9/C9 the loading was 93-96% and maximum binding was achieved in 60 mins. Increasing the incubation time to 300 mins had only a minimal improvement effect for Herceptin at pH 7.4 & 8.5 whereas increasing the incubation time for HF9/C9 had negligible effect from the binding achieved after 60 mins.

At ~pH 7.4 the HF9/C9 antibody had an improved binding capacity for the 1,3-diketoester derivatised Silica (1000 Å) over Herceptin. After 60 mins 92% of all available HF9/C9 antibody was immobilised versus 82% of Herceptin over the same time period. Over the full duration of the study this differentiation was held. In contrast, at pH 8.5 the Herceptin antibody had an improved binding over HF9/C9. After 60 mins 71% of the Herceptin was immobilised onto the derivatised silica in contrast to only 63% of the HF9/C9. Similarly, this trend held over the duration of the time course.

These differentiating effects at various pH are thought to be due to the isoelectric point of the proteins. Different antibodies exist with differing isoelectric points (P1). The isoelectric point is the pH at which the antibody has no overall charge; positive & negative charges on the molecule are equal. Therefore the net charge at a specific pH will be different for various antibodies. A antibody may be positively or negatively charged. In the results above a slightly acidic pH improves the immobilisation of Herceptin to 1,3-diketoester derivatised Silica (1000 Å) significantly.

Example 16. Cleavage of Immobilised Herceptin Antibody from Derivatised 1,3-diketoester Silica A 1.0 ml stock sample of Herceptin 150 KD antibody at a concentration of 25 mg/ml in formulation buffer was double desalted using a disposable PD-10 column containing Sephadex™ G-25 packing material (GE Healthcare, 1.45×5.0 cm (8.3 ml) packed bed dimensions). The Herceptin antibody was buffer exchanged into 30.5 ml of PBS, pH 7.4 to afford a protein concentration of 0.82 mg/ml.

A 1.22 ml solution of the 150 KD antibody Herceptin in PBS was applied to four separate 0.1 g samples of 1,3-diketoester derivatised Silica (1000 Å) for binding. The incubation was carried out at room temperature at pH 7.4 for 60 mins. The slurry was gently agitated over this duration on a roller. After the 60 mins incubation time had elapsed the silicas were washed sequentially with fresh PBS, pH 7.4. Each of the wash fractions was collected and analysed by A280 spectrophotometry for unbound antibody. Analysing the sum Abs of the wash fractions allows the accurate quantification of the quantity of Herceptin antibody immobilised onto the 1,3-diketoester derivatised Silica (1000 Å).

| Sample Number | pH | Conc. (mg/ml) | Volume charged (ml) | Herceptin unbound (Abs) | Herceptin unbound (mg) | Herceptin bound (mg) | % Locked to 1,3-diketoester Silica |
|---|---|---|---|---|---|---|---|
| 1 | 7.4 | 0.82 | 1.22 | 0.537 | 0.358 | 0.643 | 64.3 |
| 2 | 7.4 | 0.82 | 1.22 | 0.538 | 0.359 | 0.641 | 64.1 |
| 3 | 7.4 | 0.82 | 1.22 | 0.549 | 0.366 | 0.634 | 63.4 |
| 4 | 7.4 | 0.82 | 1.22 | 0.536 | 0.357 | 0.643 | 64.3 |

A series of cleavage reagents were investigated. 10 ml stock solutions of each cleavage agent were prepared as 5% v/v or w/v compositions in PBS, pH 7.4 buffer. The pH was unadjusted after the charge of the cleavage agent. The study investigated the following cleavage compositions:

5% v/v Hydrazine monohydrate in PBS
5% w/v Arginine in PBS
5% w/v Lysine in PBS
5% w/v Histidine in PBS The pH of the unadjusted cleavage mixtures was recorded and the following values were determined.

5% v/v Hydrazine monohydrate in PBS (pH 10.9)
5% w/v Arginine in PBS (pH 10.6)
5% w/v Lysine in PBS (pH 10.1)
5% w/v Histidine in PBS (pH 7.8)

Each of the four 0.1 g silica samples was treated separately with each of the cleavage mixtures above. Silica samples were incubated with cleavage mixtures for 1 hour at room temperature. The silica slurry's were gently agitated using a roller over the full duration.

The quantity of Herceptin antibody removed from the silica was determined by A280 spectrophotometry against a blank of each of the cleavage compositions. The results of the cleavage study are noted in the table below:

|  | 5% v/v Hydrazine in PBS | 5% w/v Arginine in PBS | 5% w/v Lysine in PBS | 5% w/v Histidine in PBS |
|---|---|---|---|---|
| [Herceptin] immobilised on Silica (mg) | 0.643 | 0.641 | 0.634 | 0.643 |
| A280 Release (Abs) | 0.911 | 0.940 | 0.933 | 0.464 |
| [Herceptin] cleaved in 1 hr (mg) | 0.607 | 0.627 | 0.622 | 0.309 |
| % bound material cleaved | 94.4 | 97.8 | 98.1 | 48.1 |

The results clearly indicate that the cleavage agents arginine and lysine at a 5% w/v composition in PBS are as efficient as the hydrazine monohydrate cleavage agent in the removal of Herceptin antibody, which has been immobilised to the 1,3-diketoester derivatised silica (1000 Å). Cleavage is complete within 1 hour at almost quantitative yield. The Histidine cleavage agent has not been shown to be as efficient as neither Arginine, Lysine nor Hydrazine monohydrate at unadjusted pH. The pH of the 5% w/v Histidine in PBS cleavage solution was not as basic as the other cleavage candidates. All of the cleavage reagents are composed of a primary amine necessary for nucleophilic displacement of the antibody from the 1,3-diketoester derivatised Silica (1000 Å). The results here would also indicate that a basic cleavage media enhances the cleavage of antibody from the derivatised silica support.

Example 17. Cleavage of Immobilised Herceptin Antibody from Derivatised 1,3-Diketoester Silica—Effect of Buffering pH The cleavage study from example 16 above was repeated. In this set of experiments the pH of the cleavage mixtures was adjusted to investigate the effect of pH on the cleavage of Herceptin antibody immobilised on 1,3-diketoester derivatised Silica (1000 Å).

A 1.22 ml solution of the 150 KD antibody Herceptin in PBS was applied to four separate 0.1 g samples of 1,3-diketoester derivatised Silica (1000 Å) for binding. The incubation was carried out at room temperature at pH 7.4 for 60 mins. The slurry was gently agitated over this duration on a roller. After the 60 mins incubation time had elapsed the silicas were washed sequentially with fresh PBS, pH 7.4. Each of the wash fractions was collected and analysed by A280 spectrophotometry for unbound antibody. Analysing the sum Abs of the wash fractions allows the accurate quantification of the quantity of Herceptin antibody immobilised onto the 1,3-diketoester derivatised Silica (1000 Å).

| Sample Number | pH | Conc. (mg/ml) | Volume charged (ml) | Herceptin unbound (Abs) | Herceptin unbound (mg) | Herceptin bound (mg) | % Locked to 1,3-diketoester Silica |
|---|---|---|---|---|---|---|---|
| 1 | 7.4 | 0.82 | 1.22 | 0.356 | 0.237 | 0.763 | 76.3 |
| 2 | 7.4 | 0.82 | 1.22 | 0.422 | 0.281 | 0.719 | 71.9 |
| 3 | 7.4 | 0.82 | 1.22 | 0.364 | 0.243 | 0.757 | 75.7 |
| 4 | 7.4 | 0.82 | 1.22 | 0.364 | 0.243 | 0.757 | 75.7 |

A series of cleavage reagents were investigated. 10 ml stock solutions of each cleavage agent were prepared as 5% v/v or w/v compositions in PBS, pH 7.4 buffer. The study investigated the following cleavage compositions. pH was adjusted downwards to pH 7.8 with 0.1M Acetic acid for hydrazine monohydrate, Arginine & Lysine from pH 10.9, 10.6, 10.1 respectively. Conversely, the pH of Histidine was adjusted upwards with 0.2 mM NaOH(aq.) from pH 7.8 to a final pH of 9.5. The following cleavage conditions were investigated:

5% v/v Hydrazine monohydrate in PBS (pH 7.8)
5% w/v Arginine in PBS (pH 7.8)
5% w/v Lysine in PBS (pH 7.8)
5% w/v Histidine in PBS (pH 9.5)

Each of the four 0.1 g silica samples was treated separately with each of the cleavage mixtures above. Silica samples were incubated with cleavage mixtures for 1 hour at room temperature. The silica slurry's were gently agitated using a roller over the full duration.

The quantity of Herceptin antibody removed from the silica was determined by A280 spectrophotometry against a blank of each of the cleavage compositions. The results of the cleavage study are noted in the table below:

|  | 5% v/v Hydrazine in PBS, pH 7.8 | 5% w/v Arginine in PBS, pH 7.8 | 5% w/v Lysine in PBS, pH 7.8 | 5% w/v Histidine in PBS, pH 9.5 |
|---|---|---|---|---|
| [Herceptin] immobilised on Silica (mg) | 0.763 | 0.719 | 0.757 | 0.757 |
| A280 Release (Abs) | 0.611 | 0.308 | 0.501 | 0.800 |
| [Herceptin] cleaved in 1 hr (mg) | 0.407 | 0.205 | 0.334 | 0.533 |
| % bound material cleaved | 53.3 | 28.5 | 44.1 | 70.4 |

Comparing the cleavage studies in Examples 16 & 17 would indicate that the cleavage of Herceptin antibody from 1,3-diketoester derivatised Silica (1000 Å) is enhanced by an increase in pH; towards a basic buffered environment, using the cleavage reagents hydrazine monohydrate, Arginine, Lysine & Histidine. Whilst unoptimised the results in Example 17 suggest the cleavage of Herceptin antibody may require a prolonged exposure to the cleavage agents or a second treatment with fresh cleavage agents to achieve quantitative removal from the derivatised silica support.

Example 18. Solution Phase Conjugation of Herceptin to Cytotoxin Drug-Linker vcE In this example an Antibody Drug Conjugate (ADC) will be synthesised by conjugating an antibody to a known cytotoxic moiety. vcE is an Auristatin derivative that is cytotoxic in nature. The highly potent drug component; termed MMAE (S. O. Doronina et al, Bioconjugate Chemistry, 2006, 17, 114-124), is an antimitotic agent which inhibits cell division by blocking the polymerisation of tubulin. vcE is comprised of the MMAE cytotoxic payload linked through a 'self immolative' maleimidocaproyl-valine-citrulline-p-aminobenzyloxycarbonyl linker. The maleimide group provides a reactive site for attachment through Cysteine residues on an antibody to facilitate the assembly of Antibody Drug Conjugates (ADCs). The resultant antibody-vcE antibody drug conjugate may be activated to release the cytotoxic MMAE payload via intracellular proteases such as cathepsin B which targets the 'self immolative' linker.

vcE

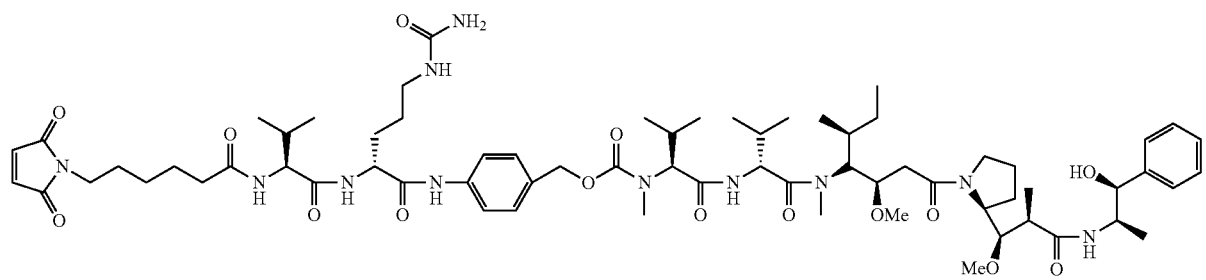

In this example the cytotoxic drug-linker vcE will be conjugated through partially reduced Herceptin to produce a model Antibody Drug Conjugate (ADC).

Preparation of Herceptin Solution—A 1.5 ml stock sample of Herceptin 150 KD antibody at a concentration of 25 mg/ml in formulation buffer was treated with 75 μl of 5% v/v 500 mM TRIS/25 mM EDTA in PBS buffer pH 8.5.

Partial reduction of immobilised Herceptin with TCEP— The antibody sample was then split equally in to three 0.5 ml aliquots in eppendorf tubes, each aliquot containing approximately 12.5 mg of Herceptin antibody. A range of charges of 10 mM TCEP reductant were dispensed to each separate Herceptin solution to afford a range of TCEP excess noted in the table below. The resultant mixtures were then incubated for 90 mins with gentle agitation at room temperature.

Conjugation of cytotoxic drug-linker (vcE)—To each of the three samples was charged a single aliquot of the cytotoxic drug-linker vcE. The volume of 10 mM vcE solution in DMSO dispensed to each sample is noted in the table below. Additional DMSO solvent was then added to each of the three conjugation reactions to afford a total solvent volume of 50 μl.

| Aliquot Number | Mass of Her (mg) | MW of HER | Excess of TCEP | Volume of 10 mM TCEP (μL) | Volume of 10 mM vcE (μL) |
|---|---|---|---|---|---|
| 1 | 12 | 145167 | 0.5 | 4.1 | 10.3 |
| 2 | 12 | 145167 | 1 | 8.3 | 20.7 |
| 3 | 12 | 145167 | 2 | 16.5 | 41.3 |

The conjugation reactions were performed over a 30 minute duration at room temperature. Gentle agitation was achieved on a roller. After this duration a 2 ml charge of PBS buffer pH7.4 was added to each sample. The three resultant solution phase conjugates were then separately desalted using a disposable PD-10 column containing Sephadex™ G-25 packing material (GE Healthcare, 1.45×5.0 cm (8.3 ml) packed bed dimensions). The 2.5 ml charge of antibody drug conjugate was run into the resin. The filtrate was discarded. A single 0.5 ml charge of fresh PBS pH 7.4 was added to the column. The filtrate was once again discarded. A final 2.5 ml flush with fresh PBS pH 7.4 was added to the column and the filtrate collected. The PD-10 desalt column removes the excess free vcE drug-linker.

Each of the three antibody drug conjugate products was analysed by Hydrophobic Interaction Chromatography (HIC) using the conditions noted below. A standard of double desalted Herceptin was analysed simultaneously as a reference.

HIC Methodology:
Column: TOSOH Bioscience Butyl-NPR 4.6 mm i.d.× 35.5 mm, 2.5 μm
Buffer A: 1.5M $(NH_4)_2SO_4$, 25 mM $NaH_2PO_4$ pH 6.95
Buffer B: 75% 25 mM $NaH_2PO_4$ pH 6.95: 25% Isopropyl alcohol (IPA)
Flow: 0.8 ml/min
Load: 10 μl
Wavelength of analysis: 280 nm
Gradient: 0% B to 100% B over 12 minutes
Temp: Ambient (24° C.)

The HIC elution profiles clearly note the conversion of native Herceptin antibody to several new more hydrophobic species. Conjugation to vcE was demonstrated by the gradual consumption of Herceptin (Rt 4.6 mins, non-reduced, DAR=0) and the concurrent formation of new elution peaks at Rt 6.1, 7.9 (& a minor peak at Rt 8.0) mins respectively. As the TCEP equivalents were increased there was a notable trend in the disappearance of Herceptin at Rt 4.6 and an increase in the peaks at Rt 6.1 & 7.9 mins. The new elution peaks denote new DAR species.

Example 19. Solid Phase Conjugation of Herceptin to Cytotoxin Druq-Linker vcE

Preparation of double desalted Herceptin—A 2.5 ml stock sample of Herceptin 150 KD antibody at a concentration of 25 mg/ml in formulation buffer was double desalted using a disposable PD-10 column containing Sephadex™ G-25 packing material (GE Healthcare, 1.45×5.0 cm (8.3 ml) packed bed dimensions). The Herceptin antibody was buffer exchanged into PBS, pH 7.4 to afford a Herceptin stock solution with protein concentration of 8.56 mg/ml. A 1 mg/ml Herceptin solution in PBS pH 7.4 was prepared using this double desalted stock solution by dilution with PBS, pH 7.4.

Immobilisation of Herceptin to 1,3-diketoester derivatised silica—1 ml of the 150 KD antibody Herceptin at concentration 1 mg/ml was applied to five separate 0.1 g samples of 1,3-diketoester derivatised Silica (1000 Å) in PBS for binding. The incubation was performed at pH 7.4 at room temperature over an 18 hr duration. Herceptin antibody binding was monitored spectrophotometrically by A280. After 18 hours each of the individual silicas were pelleted and an 800 μl sample was taken from each and analysed by A280 to determine concentration of unbound Herceptin. The derivatised silicas were then washed sequentially with 2×1 ml aliquots of fresh PBS, pH 7.4. Each wash fraction was also collected and analysed for Herceptin content by A280. The A280 analysis determined that Herceptin was present in both the initial 800 μl sample and the first 1 ml wash fraction. These values were combined to determine the total concentration of Herceptin unbound (and hence bound) to the silica. For the five individual samples the Herceptin immobilised was very reproducible giving a range of between 0.835 to 0.849 mg of Herceptin bound per 0.1 g of 1,3-diketoester derivatised Silica (1000 Å).

| | Experiment | | | | |
|---|---|---|---|---|---|
| | 1 | 2 | 3 | 4 | 5 |
| Silica (mg) | 100 | 100 | 100 | 100 | 100 |
| volume of 1 mg/ml Her added | 1 | 1 | 1 | 1 | 1 |
| A280 Post Bind Abs (800 µl) | 0.174 | 0.180 | 0.192 | 0.171 | 0.165 |
| mg of herceptin Post Bind (800 µl) | 0.093 | 0.096 | 0.102 | 0.091 | 0.088 |
| A280 wash sample Abs (1 ml) | 0.087 | 0.096 | 0.094 | 0.089 | 0.096 |
| mg of herceptin in wash | 0.058 | 0.064 | 0.063 | 0.059 | 0.064 |
| Estimate of mass of Her unBound (mg) | 0.151 | 0.160 | 0.165 | 0.151 | 0.152 |
| Estimate of mass of Her Bound | 0.849 | 0.840 | 0.835 | 0.849 | 0.848 |
| % of herceptin bound | 84.9 | 84.0 | 83.5 | 84.9 | 84.8 |

Partial reduction of immobilised Herceptin with TCEP—Silica with immobilised Herceptin antibody was suspended in 1 ml pBS at pH 7.4 within an eppendorf. A 1 mM TCEP solution was then charged to each of the five silica samples to give a range of TCEP molar excesses defined in the table below. Each individual reaction was then incubated at room temperature for 1 hour and agitated gently on a roller.

| | TCEP Molar Excess | | | | |
|---|---|---|---|---|---|
| | 1 | 1.50 | 2.00 | 2.50 | 3.00 |
| Volume 1 mM TCEP (L) | 5.5 | 8.3 | 11 | 13.8 | 16.5 |

Conjugation of cytotoxic drug-linker (vcE)—A 1 mM solution of vcE in DMSO was charged to each of the five individual reactions following the definitions noted in the table below. The resultant suspensions were then incubated for a further 1 hour at room temperature to facilitate coupling of the vcE drug-linker to the immobilised partially reduced Herceptin. After 1 hour the silica was pelleted and the supernatant removed from each of the five individual samples. Each sample was quenched by the addition of 1 mM N-acetyl cysteine (NAC, 5 µl) to neutralise the maleimide croup on the vcE drug-linker.

| | TCEP Excess | | | | |
|---|---|---|---|---|---|
| | 1 | 1.50 | 2.00 | 2.50 | 3.00 |
| Volume 1 mM TCEP (µL) | 5.5 | 8.3 | 11 | 13.8 | 16.5 |
| Volume of 1 mM vcE (µL) | 15 | 25 | 35 | 45 | 55 |
| Volume of 0.1M NAC quenching agent (µL) | 5 | 5 | 5 | 5 | 5 |

Quenched free drug was collected for analysis. The silica was then washed sequentially with 2×1 ml portions of PBS, pH 7.4 to ensure all free drug has been removed from the silica. The final wash was decanted from the silica to leave a damp pellet of silica.

Cleavage of vcE-Herceptin conjugate from silica—A stock solution of 10 ml of 5% v/v Hydrazine monohydrate solution was prepared in PBS pH7.4. The pH was unadjusted after addition of the hydrazine. 1 ml of 5% v/v Hydrazine monohydrate solution in PBS was charged to each of the five washed silica samples. The resultant suspensions were then incubated at room temperature for 90 minutes. Each of the five silicas were pelleted and the supernatants collected. Each silica was then washed sequentially with 2×1 ml portions of fresh PBS at pH 7.4. Each of these individual wash fractions were collected and analysed by A280 to determine Herceptin concentration [HER]. Cleaved fractions from each of the five samples were combined and then purified using a disposable PD-10 column containing Sephadex™ G-25 packing material.

G25 purification—Each of the five vcE-Her conjugates were collected from the G25 column in three fractions. Initially 1 ml of PBS pH 7.4 was applied to the column and eluent collected. This was followed by the application of 2.5 ml of PBS pH 7.4 which was collected in a separate vessel. Finally the column was washed with a final 1 ml of PBS pH 7.4 which was also collected. The three fractions were analysed by A280 nm to determine the concentration of HER cleaved. The 2.5 ml fraction was also analysed at A250 nm.

| A280 pre G25 | 0.703 | 0.536 | 0.557 | 0.454 | 0.581 |
|---|---|---|---|---|---|
| A280 post G25 first 1 ml fraction | 0.102 | 0.084 | 0.119 | 0.07 | 0.075 |
| A280 post G25 final 1 ml fraction | 0.032 | 0.035 | 0.019 | 0.027 | 0.023 |
| A280 post G25 concentrated 2.5 ml fraction | 0.23 | 0.231 | 0.186 | 0.161 | 0.133 |
| A250 post G25 concentrated 2.5 ml fraction | 0.087 | 0.104 | 0.1 | 0.087 | 0.077 |
| A250/A280 | 0.378 | 0.450 | 0.538 | 0.540 | 0.579 |
| total mg of Ab | 0.47 | 0.46 | 0.40 | 0.33 | 0.29 |
| % Ab yield based on total Ab bound | 55.66 | 55.28 | 48.15 | 39.20 | 33.84 |

Each of the five antibody drug conjugate samples was concentrated using a Vivaspin™ columns with MW 50000 cut-off. Each conjugate sample was subsequently mobilised in 100 µl of PBS buffer pH 7.4 for HIC analysis.

ID by OD—see FIGS. 11 and 12

FIG. 11 illustrates the linear relationship between UV absorbance at 250 nm (normalised at 280 nm) and TCEP molar excess. With an excess of vcE drug-linker all free thiols groups generated from the TCEP reduction are converted to conjugate. The absorbance at 250 nm is characteristic for the vcE drug-linker and thus the degree of conjugation—referred to as the Drug Antibody Ratio (DAR).

FIG. 12 demonstrates the relationship between TCEP and DAR. The UV spectra scan (relative to normalised 280 nm absorbance) illustrates the increase in drug specific absorbance at 254 nm as TCEP and vcE drug-linker excess are increased.

The yield of vcE-Herceptin conjugates obtained ranged between 34-55%. The quantity of cleaved appeared dependent on the amount of TCEP and drug linker, with lower yield obtained as the concentrations of these were increased.

Hydrophobic Interaction Chromatography (HIC)

HIC analysis is an adsorptive liquid chromatography technique that separates biomolecules according to hydrophobicity. Proteins such as antibodies are composed of hydrophilic and hydrophobic amino acid side chains. The vast majority of hydrophobic amino acids are buried deep within the tertiary structure of the protein; however; some hydrophobic amino acids are present and distributed upon the protein surface. HIC exploits the hydrophobic surface properties of proteins through an attraction of these surface amino acids to the relatively mild hydrophobic surface of a HIC stationary support (at high salt concentrations in an aqueous environment). By decreasing the salt concentration the attraction between protein and the hydrophobic ligands of the HIC stationary phase is reduced. At negligible salt concentrations the interaction is completely removed. The amount of exposed hydrophobic amino acids differs between proteins and so does the ability of proteins to interact with HIC stationary supports. Typically analysis is performed at 280 nm.

A simple indication of the conjugation of a drug linker to an antibody can be demonstrated using HIC analysis. By analysing a standard of an antibody at a known concentration HIC will determine the retention time of the antibody and also the peak area at this concentration. The retention time will be characteristic for the antibody. An elution profile can therefore be generated for the antibody. Subsequently, taking the antibody through a typical conjugation reaction wherein the antibody is subject to either partial reduction (TCEP) or derivatisation of Lysine (Traut's Reagent) then reacted with a drug-linker the physiochemical characteristics of the antibody will change. As the antibody reacts with drug-linker the newly formed conjugate increases in hydrophobicity compared to the antibody alone. Characteristically, this increase in hydrophobicity is indicated by an increase in retention time for the conjugate and the simultaneous reduction/disappearance of the antibody starting material from the elution profile. Therefore, HIC analysis affords a simple indication that a conjugation has been successful.

HIC analysis is utilised to determine the drug antibody ratio (DAR) of a conjugate and may also be applied to qualify the extent of free drug-linker in the product. Specifically for the drug-linker vcE HIC is particularly useful using a method referred to as 'ID-by-OD'. The carbamate group of the vcE drug-linker specifically absorbs at a wavelength of 254 nm. In contrast protein absorbs characteristically at 280 nm and contributes minimally at 254 nm. Therefore, UV absorption at 254 nm can be attributed to the vcE drug-linker. Therefore, in an antibody conjugate containing the vcE drug-linker there is a direct linear relationship between A280 & A254 scans. As the DAR increases the quantity of drug linker in the conjugate increases according therefore increasing the absorbance signal at 254 nm in a linear fashion. This relationship can be demonstrated by purposefully synthesising a series of antibody-vcE conjugates with a range of DARs. A plot of UV absorbance against wavelength (normalised at 280 nm) clearly indicates increases in absorbance at 254 as DAR increases. Such a plot can be used as a basic visual indication of successful conjugation of vcE (M. M. C. Sun et al, Bioconjugate Chemistry, 2005, 16, 1282-1290, S. O. Doronina et al, Bioconjugate Chemistry, 2006, 17, 114-124).

HIC can also be utilised to demonstrate the direct relationship between TCEP and DAR. In our conjugation experiments there is an assumption that all the TCEP reductant has been utilised to generate free thiol on the antibody. It is free thiol that binds to the maleimide group on the vcE drug-linker. One mole of TCEP will generate two moles of thiol as one disulphide bond is broken. The conjugations in Examples 18 & 19 were ensured an excess of vcE drug-linker by adding 2.5 mole equivalents of drug-linker per mole of TCEP. Therefore, if maximum 100% utility of the TCEP reductant was achieved the vcE drug-linker would be assured at 125% of potential free thiol.

In Example 19 following treatment with TCEP and gel permeation chromatography with PD-10 columns to remove the excess residual drug-linker the UV spectra scan (relative to normalised 280 nm absorbance) clearly demonstrated an increase in drug specific absorbance at 254 nm as TCEP and vcE drug-linker excess are increased (see FIG. 12). This trend for vcE conjugates is well known in the literature (Nathan Ihle, Seattle Genetics, Proceedings from 17th WCBP CMC Strategy Forum, 24 Jan. 2010, Presentation 'Analytical Characterization and Scale-up for Brentuximab Vedotin [SGN-35]').

HIC Methodology

Column: TOSOH Bioscience Butyl-NPR 4.6 mm i.d.× 35.5 mm, 2.5 µm

Buffer A: 1.5M $(NH_4)_2SO_4$, 25 mM $NaH_2PO_4$ pH 6.95

Buffer B: 75% 25 mM $NaH_2PO_4$ pH 6.95: 25% Isopropyl alcohol (IPA)

Flow: 0.8 ml/min

Gradient: 0% B to 100% B over 12 minutes

Load: 10 µl

Wavelength of analysis: 280 nm

Temp: Ambient (24° C.)

In an identical manner to HIC data obtained in Example 18 the elution profiles clearly note the conversion of native Herceptin antibody to several new more hydrophobic species. Conjugation to vcE was demonstrated by the gradual consumption of Herceptin (Rt 4.6 mins, non-reduced, DAR=0) as the TCEP equivalents were increased and the appearance of new elution peaks at Rt 6.2 & 7.9 (& a minor peak at Rt 5.2) mins respectively. The new peaks denote new DAR species.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method for binding a biomolecule, wherein the biomolecule comprises at least one primary amine group, to a support, the method comprising the step of:

contacting a solution of the biomolecule with a mobile or immobilised support comprising one or more functional groups independently selected from 1,3-ketoesters, 1,3-ketothioesters or 1,3-ketoamides to form a covalently bound support-biomolecule compound, wherein the 1,3-ketoester, 1,3-ketothioester or 1,3-ketoamide is a group of Formula 1:

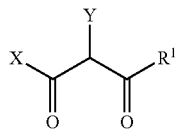

Formula 1

Wherein R¹ is an optionally substituted hydrocarbyl, perhalogenated hydrocarbyl, or a heterocyclyl group;

Y is hydrogen, an optionally substituted hydrocarbyl, or a heterocyclyl group;

X is —O—, —NR$_2$ or —S—, wherein the free valence of —O—, —NR$_2$ or —S— is bonded to the support optionally via a linker; and R² is hydrogen, an optionally substituted hydrocarbyl, or a heterocyclyl group;

wherein the biomolecule is selected from the group consisting of: antibodies, antibody fragments, modified antibodies, antibody-drug conjugates, enzymes, proteins, peptides, polypeptides, modified peptides, peptide nucleic acids (PNAs), metalloproteins, peptide-drug conjugates, peptide-oligonucleotide hybrids, amino acids, non-naturally occurring amino acids, diamino acids, synthetic amino acids, amino acid-drug conjugates, oligonucleotides, modified oligonucleotides, oligonucleotides-drug conjugates, nucleotides, nucleosides, purines, pyrimidines, oligosaccharides, polysaccharide, disaccharides, monosaccharides, amino sugars, lipids, phospholipids, glycolipids, sterols, vitamins, hormones, neurotransmitters, carbohydrates, sugars, viruses, cells and active pharmaceutical ingredients (APIs).

2. The method of claim 1, wherein the method further comprises the step of washing the support-biomolecule compound.

3. The method of claim 1, wherein the method further comprises the step of releasing the biomolecule from the support-biomolecule compound and recovering the biomolecule; and optionally recovering the support.

4. The method of claim 1, wherein the method further comprises the steps of carrying out one or more chemical reactions on the support-biomolecule compound to synthesise support-biomolecule-drug compound;

optionally washing the support-biomolecule-drug compound; and releasing a biomolecule-drug compound from the support-biomolecule-drug compound, optionally, the method further comprises the step of recovering the support.

5. The method of claim 1, wherein the method further comprises the step of
drying the support-biomolecule compound;
optionally, the method further comprises the step of releasing the biomolecule from the support-biomolecule compound and recovering the biomolecule.

6. The method of claim 1, wherein the support is a bead with a diameter of 10 μm to 2000 μm or is selected from the group consisting of polyethylene, poly(tetrafluoroethylene), polymethacrylate, functionalised monolith, a functionalised fibre, monolithic columns, agarose, sepharose, cellulose, Kieselguhr, Controlled Pore Glass (CPG) beads, magnetic recoverable polymer beads, polyethylene glycol, polyacrylamide, polyethylene glycol grafted to polystyrene, polystyrene (PS-DVB), silica, polystyrene, Davisil LC1000 Å, MS-Gel D-50-1000 Å, QuadraPure BZA, Hydroxymethyl PS, Aminomethyl PS, and NovaSyn TentaGel.

7. The method of claim 3, wherein the step of releasing the biomolecule from the support is selected from:
   a) exposing the support-biomolecule to a release agent; and
   b) altering the pH to break the support-biomolecule bond.

8. The method of claim 1, wherein the release agent is a primary amine selected from the group consisting of lysine, hydroxylamine, hydrazine and ethanolamine; or wherein the release agent is a nucleophile that is selected from the group consisting of hydroxylamine and ammonia.

9. The method of claim 1, wherein the pH is increased to being greater than pH 8.

10. The method of claim 1, wherein the functional group is a 1,3-ketoamide.

11. The method of claim 1, wherein the functional group is a 1,3-ketoester, 1,3-ketothioesters, 1,3-ketoamides, or mixtures thereof.

12. The method of claim 1, wherein:
R¹ is a C1-4 alkyl group, preferably a methyl group;
Y is hydrogen;
R² is hydrogen or a C1-4 alkyl group;
X is —O—, —NH—, or S.

13. The method of claim 1, wherein the covalent bond between the support and the biomolecule is an enamine bond.

14. The method of claim 1, wherein the support is a polymer comprising one or more polymerisable monomers wherein the monomer is selected from the group consisting of styrene and substituted styrenes; alkyl esters of mono-olefinically unsaturated dicarboxylic acids; vinyl esters of carboxylic acids and vinyl esters of versatic acid; acrylamides; methacrylamides; nitrile monomers; esters of acrylic and methacrylic acid; divinylbenzene; trivinylbenzene; multifunctional acrylates; methacrylates; polyethers or silica; or is a polymer selected from the group consisting of polyethylene glycol (PEG), polyethylene glycol grafted polystyrene CPSPEG co-polymer), polypropylene, poly(tetrafluoroethylene) and polyethylene.

15. The method of claim 1, wherein the biomolecule is an antibody.

* * * * *